US008178577B2

(12) United States Patent
Lu et al.

(10) Patent No.: US 8,178,577 B2
(45) Date of Patent: May 15, 2012

(54) TRICYCLIC DERIVATIVES AS POTENT AND SELECTIVE HISTONE DEACETYLASE INHIBITORS

(75) Inventors: Xian-Ping Lu, Belle Meade, NJ (US); Zhi-Bin Li, Shenzhen (CN); Zhi-Qiang Ning, Shenzhen (CN)

(73) Assignee: Shenzhen Chipscreen Biosciences Ltd., Shenzhen (CN)

( * ) Notice: Subject to any disclaimer, the term of this patent is extended or adjusted under 35 U.S.C. 154(b) by 354 days.

(21) Appl. No.: 12/463,176

(22) Filed: May 8, 2009

(65) Prior Publication Data

US 2009/0292001 A1    Nov. 26, 2009

Related U.S. Application Data

(60) Provisional application No. 61/054,976, filed on May 21, 2008.

(51) Int. Cl.
| | |
|---|---|
| A61K 31/382 | (2006.01) |
| A61K 31/352 | (2006.01) |
| A61K 31/16 | (2006.01) |
| C07D 335/02 | (2006.01) |
| C07D 311/82 | (2006.01) |
| C07C 233/00 | (2006.01) |

(52) U.S. Cl. ......... 514/437; 514/454; 514/616; 549/13; 549/388; 564/158

(58) Field of Classification Search .................. None
See application file for complete search history.

(56) References Cited

U.S. PATENT DOCUMENTS

| 7,569,724 B2 * | 8/2009 | Watkins et al. ............... 564/155 |
| 2002/0103192 A1 | 8/2002 | Curtin et al. |
| 2004/0092598 A1 * | 5/2004 | Watkins et al. ............... 514/575 |

FOREIGN PATENT DOCUMENTS

| EP | 0847992 A1 | 6/1998 |
| WO | WO0118171 A2 | 3/2001 |
| WO | WO0170675 A2 | 9/2001 |
| WO | WO0226696 A1 | 4/2002 |

OTHER PUBLICATIONS

Grunstein, M., "Histone Acetylation in Chromatin Structure and Transcription", Nature, (1997), vol. 389, pp. 349-352.
de Ruijter, A. J. M., et al, "Histone Deacetylases (HDACs): Characterization of the Classical HDAC Family", Biochemical Journal, (2003), vol. 370, pp. 737-749.
Grignani, F. et al., "Fusion Proteins of the Retinoic Acid Receptor-α Recruit Histone Deacetylase in Promyelocytic Leukaemia", Nature, (1998), vol. 391, pp. 815-818.
Lin, R. J. et al., "Role of the Histone Deacetylase Complex in Acute Promyelocytic Leukaemia", Nature, (1998), vol. 391, pp. 811-814.
Marks, P.-A., et al., "Histone Deacetylases and Cancer: Causes and Therapies", Nature Reviews Cancer, (2001), vol. 1, pp. 194-202.
Langley, B. et al., "Remodeling Chromatin and Stress Resistance in the Central Nervous System: Histone Deacetylase Inhibitors as Novel and Broadly Effective Neuroprotective Agents", Current Drug Targets—CNS & Neurological Disorders, (2005), vol. 4, pp. 41-50.
Dokmanovic, M. et al., "Prospects: Histone Deacetylase Inhibitors", Journal of Cellular Biochemistry, (2005), vol. 96, pp. 293-304.
Fischer A., et al., "Recovery of Learning and Memory is Associated with Chromatin Remodelling", Nature, (2007), vol. 447, pp. 178-183.
Herman, D. et al., "Histone Deacetylase Inhibitors Reverse Gene Silencing in Friedreich's Ataxia", Nature Chemical Biology, (2006), vol. 2, No. 10, pp. 551-559.
Glaser, K. B. et al., "Role of Class I and Class II Histone Deacetylases in Carcinoma Cells Using siRNA", Biochemical and Biophysical Research Communications, (2003), vol. 310, No. 2, pp. 529-536.
Lagger, G. et al., "Essential Function of Histone Deacetylase 1 in Proliferation Control and CDK Inhibitor Repression", The EMBO Journal, (2002), vol. 21, No. 11, pp. 2672-2681.
Bartl, S. et al., "Identification of Mouse Histone Deacetylase 1 as a Growth Factor-Inducible Gene", Molecular and Cellular Biology, (1997), vol. 17, No. 9, pp. 5033-5043.
Trivedi, C. M. et al., "Hdac2 Regulates the Cardiac Hypertrophic Response by Modulating Gsk3β Activity", Nature Medicine, (2007), vol. 13, No. 3, pp. 324-331.
Wilson, A-J. et al., "Histone Deacetylase 3(HDAC3) and Other Class I HDACs Regulate Colon Cell Maturation and p21 Expression and Are Deregulated in Human Colon Cancer", The Journal of Biological Chemistry, (2006), vol. 281, No. 19, pp. 13548-13558.
Sakuma, T. et al., "Aberrant Expression of Histone Deacetylase 6 in Oral Squamous Cell Carcinoma", International Journal of Oncology, (2006), vol. 29, pp. 117-124.
Pandey U. B., et al, "HDAC6 Rescues Neurodegeneration and Provides an Essential Link Between Autophagy and the UPS", Nature, (2007), vol. 447, pp. 859-863.
Martin M. et al, "Class IIa Histone Deacetylases: Regulating the Regulators", Oncogene, (2007), vol. 26, pp. 5450-5467.
Glaros, S. et al., "The Reversible Epigenetic Silencing of BRM: Implications for Clinical Targeted Therapy", Oncogene, (2007), vol. 26, pp. 7058-7066.
Mai, A. et al., "Novel Pyrrole-Containing Histone Deacetylase Inhibitors Endowed with Cytodifferentiation Activity", The International Journal of Biochemistry & Cell Biology, (2007), vol. 39, pp. 1510-1522.
Vincent, A. et al., "Epigenetic Regulation(DNA Methylation, Histone Modifications) of the 11p15 Mucin Genes (MUC2, MUC5AC, MUC5AC, MUC5B, MUC6) in Epithelial Cancer Cells", Oncogene, (2007), vol. 26, pp. 6566-6576.

(Continued)

*Primary Examiner* — Kamal Saeed
(74) *Attorney, Agent, or Firm* — Eckert Seamans Cherin & Mellott, LLC

(57) ABSTRACT

The present invention relates to certain tricyclic derivatives which are capable of inhibiting histone deacetylases. The compounds of this invention are therefore useful in treating diseases associated with abnormal histone deacetylase activities. Pharmaceutical compositions comprising these compounds, methods of treating diseases utilizing pharmaceutical compositions comprising these compounds, and methods of preparing these compounds are also disclosed.

9 Claims, No Drawings

OTHER PUBLICATIONS

Avila, A. M. et al., "Trichostatin A Increases SMN Expression and Survival in a Mouse Model of Spinal Muscular Atrophy", The Journal of Clinical Investigation, (2007), vol. 117, No. 3, pp. 659-671.

De Boer, J. et al., "Inhibition of Histone Acetylation as a Tool in Bone Tissue Engineering", Tissue Engineering, (2006), vol. 12, No. 10, pp. 2927-2937.

Gialitakis, M. et al., "Coordinated Changes of Histone Modifications and HDAC Mobilization Regulate the Induction of MHC Class II Genes by Trichostatin A", Nucleic Acids Research, (2006), vol. 34, No. 3, pp. 765-772.

* cited by examiner

TRICYCLIC DERIVATIVES AS POTENT AND SELECTIVE HISTONE DEACETYLASE INHIBITORS

FIELD OF INVENTION

The present invention relates to certain tricyclic derivatives which are capable of inhibiting histone deacetylases. The compounds of this invention are therefore useful in treating diseases associated with abnormal histone deacetylase activities. Pharmaceutical compositions comprising these compounds, methods of treating diseases utilizing pharmaceutical compositions comprising these compounds, and methods of preparing these compounds are also disclosed.

BACKGROUND OF THE INVENTION

Histone deacetylase (HDAC) proteins play a critical role in regulating gene expression in vivo by altering the accessibility of genomic DNA to transcription factors. Specifically, HDAC proteins remove the acetyl group of acetyl-lysine residues on histones, which can result in nucleosomal remodeling (Grunstein, M., 1997, *Nature*, 389: 349-352). Due to their governing role in gene expression, HDAC proteins are associated with a variety of cellular events, including cell cycle regulation, cell proliferation, differentiation, reprogramming of gene expression, and cancer development (Ruijter, A-J-M., 2003, *Biochem. J.*, 370: 737-749; Grignani, F., 1998, *Nature*, 391: 815-818; Lin, R-J., 1998, 391: 811-814; Marks, P-A., 2001, *Nature Reviews Cancer*, 1: 194). The aberrant deacetylation resulting from the misregulation of histone deacetylases (HDACs) has been linked to clinical disorders such as Rubinstein-Taybi syndrome, fragile X syndrome, leukemia, and various cancers (Langley B et al., 2005, *Current Drug Targets—CNS & Neurological Disorders*, 4: 41-50). In fact, HDAC inhibitors have been demonstrated to reduce tumor growth in various human tissues and in animal studies, including lung, stomach, breast, and prostrate (Dokmanovic, M., 2005, *J. Cell Biochem.*, 96: 293-304).

The aberrant histone deacetylase activity has also been linked to various neurological and neurodegenerative disorders, including stroke, Huntington's disease, Amyotrophic Lateral Sclerosis and Alzheimer's disease. HDAC inhibition may induce the expression of anti-mitotic and anti-apoptotic genes, such as p21 and HSP-70, which facilitate survival. HDAC inhibitors can act on other neural cell types in the central nervous system, such as reactive astrocytes and microglia, to reduce inflammation and secondary damage during neuronal injury or disease. HDAC inhibition is a promising therapeutic approach for the treatment of a range of central nervous system disorders (Langley B et al., 2005, *Current Drug Targets—CNS & Neurological Disorders*, 4: 41-50).

Mammalian HDACs can be divided into three classes according to sequence homology. Class I consists of the yeast Rpd3-like proteins (HDAC 1, 2, 3, 8 and 11). Class II consists of the yeast HDA1-like proteins (HDAC 4, 5, 6, 7, 9 and 10). Class III consists of the yeast SIR2-like proteins (SIRT 1, 2, 3, 4, 5, 6 and 7).

The activity of HDAC1 has been linked to cell proliferation, a hallmark of cancer. Particularly, mammalian cells with knock down of HDAC1 expression using siRNA were antiproliferative (Glaser, K-B., 2003, *Biochem. Biophys. Res. Comm.*, 310: 529-536). While the knock out mouse of HDAC1 was embryonic lethal, the resulting stem cells displayed altered cell growth (Lagger, G., 2002, *EMBO J.*, 21: 2672-2681). Mouse cells overexpressing HDAC1 demonstrated a lengthening of $G_2$ and M phases and reduced growth rate (Bartl. S., 1997, Mol. Cell. Biol., 17: 5033-5043). Therefore, the reported data implicate HDAC1 in cell cycle regulation and cell proliferation.

HDAC2 regulates expression of many fetal cardiac isoforms. HDAC2 deficiency or chemical inhibition of histone deacetylase prevented the re-expression of fetal genes and attenuated cardiac hypertrophy in hearts exposed to hypertrophic stimuli. Resistance to hypertrophy was associated with increased expression of the gene encoding inositol polyphosphate-5-phosphatase f (Inpp5f) resulting in constitutive activation of glycogen synthase kinase 3β (Gsk3β) via inactivation of thymoma viral proto-oncogene (Akt) and 3-phosphoinositide-dependent protein kinase-1 (Pdk1). In contrast, HDAC2 transgenic mice had augmented hypertrophy associated with inactivated Gsk3β. Chemical inhibition of activated Gsk3β allowed HDAC2-deficient adults to become sensitive to hypertrophic stimulation. These results suggest that HDAC2 is an important molecular target of HDAC inhibitors in the heart and that HDAC2 and Gsk3β are components of a regulatory pathway providing an attractive therapeutic target for the treatment of cardiac hypertrophy and heart failure (Trivedi, C-M., 2007, *Nat. Med.* 13: 324-331).

HDAC3 are maximally expressed in proliferating crypt cells in normal intestine. Silencing of HDAC3 expression in colon cancer cell lines resulted in growth inhibition, a decrease in cell survival, and increased apoptosis. Similar effects were observed for HDAC2 and, to a lesser extent, for HDAC1. HDAC3 gene silencing also selectively induced expression of alkaline phosphatase, a marker of colon cell maturation. Concurrent with its effect on cell growth, overexpression of HDAC3 inhibited basal and butyrate-induced p21 transcription in a Sp1/Sp3-dependent manner, whereas silencing of HDAC3 stimulated p21 promoter activity and expression. These findings identify HDAC3 as a gene deregulated in human colon cancer and as a novel regulator of colon cell maturation and p21 expression (Wilson, A-J., 2006, *J. Biol. Chem.*, 281: 13548-13558).

HDAC6 is a subtype of the HDAC family that deacetylates alpha-tubulin and increases cell motility. Using quantitative real-time reverse transcription polymerase chain reaction and Western blots on nine oral squamous cell carcinoma (OSCC)-derived cell lines and normal oral keratinocytes (NOKs), HDAC6 mRNA and protein expression were commonly up-regulated in all cell lines compared with the NOKs. Immunofluorescence analysis detected HDAC6 protein in the cytoplasm of OSCC cell lines. Similar to OSCC cell lines, high frequencies of HDAC6 up-regulation were evident in both mRNA (74%) and protein (51%) levels of primary human OSCC tumors. Among the clinical variables analyzed, the clinical tumor stage was found to be associated with the HDAC6 expression states. The analysis indicated a significant difference in the HDAC6 expression level between the early stage (stage I and II) and advanced-stage (stage III and IV) tumors (P=0.014). These results suggest that HDAC6 expression may be correlated with tumor aggressiveness and offer clues to the planning of new treatments (Sakuma, T., 2006, *Int. J. Oncol.*, 29: 117-124).

Epigenetic silencing of functional chromosomes by HDAC is one of the major mechanisms that occurs in pathological processes in which functionally critical genes are repressed or reprogrammed by HDAC activities, leading to the loss of phenotypes in terminal differentiation, maturation and growth control, and the loss of functionality of tissues. For example, tumor suppressor genes are often silenced during development of cancer and chemical inhibitors of HDAC can derepress the expression of these tumor suppressor genes, leading to growth arrest and differentiation (Glaros S et al., 2007, Oncogene June 4 Epub ahead of print; Mai, A, et al., 2007, Int J. Biochem Cell Bio., April 4, Epub ahead of print; Vincent A. et al., 2007, Oncogene, April 30, Epub ahead of print; our unpublished results). Repression of structural genes such as FXN in Friedreich's ataxia and SMN in spinal muscular atrophy can be reversed by HDAC inhibitors, leading to re-expression and resumption of FXN and SMN gene function in tissues (Herman D et al., 2006, Nature Chemical Biology, 2(10):551-8; Avila A M et al., 2007, J Clinic Investigation, 117(3)659-71; de Bore J, 2006, Tissue Eng. 12(10): 2927-37); Induction of the entire MHC II family gene expression through reprogramming of HDAC "hot spot" in chromosome 6p21-22 by HDAC inhibitors further extends epigenetic modulation of immune recognition and immune response (Gialitakis M et al., 2007, Nucleic Acids Res., 34(1); 765-72).

Several classes of HDAC inhibitors have been identified, including (1) short-chain fatty acids, e.g. butyrate and phenylbutyrate; (2) organic hydroxamic acids, e.g. suberoylanilide hydroxamic acid (SAHA) and trichostatin A (TSA); (3) cyclic tetrapeptides containing a 2-amino-8-oxo 9,10-expoxydecanoyl (AOE) moiety, e.g. trapoxin and HC-toxin; (4) cyclic peptides without the AOE moiety, e.g. apicidin and FK228; and (5) benzamides, e.g. MS-275 (EP0847992A1, US2002/0103192A1, WO02/26696A1, WO01/70675A2, WO01/18171A2). HDAC represents a very promising drug target especially in the context of epigenetic biology; for example, in terms of preferential apoptosis-induction in malignant cells but not normal cells, differentiation of epithelia in cancer cells, anti-inflammatory and immunomodulation, and cell cycle arrest.

The use of HDAC inhibitors can be considered as "neo-chemotherapy" having a much improved toxicity profile over existing chemotherapy options. The success of SAHA from Merck is currently only limited to the treatment of cutaneous T cell lymphoma. No reports exist indicating that SAHA treatment is effective against major solid tumors or for any other indications. Therefore, there is still a need to discover new compounds with improved profiles, such as stronger HDAC inhibitory activity and anti-cancer activity, more selective inhibition on different HDAC subtypes, and lower toxicity; There is also a continuing need to identify novel HDAC inhibitors that can be used to treat potential new indications such as neurological and neurodegenerative disorders, cardiovascular disease, metabolic disease, and inflammatory and immunological diseases.

SUMMARY OF THE INVENTION

The present invention is directed to certain tricyclic derivatives which exhibit selective histone deacetylase inhibition activity and are therefore useful in treating diseases associated with aberrant histone deacetylase activities, such as Rubinstein-Taybi syndrome, fragile X syndrome, leukemia, cancer and various neurological and neurodegenerative disorders.

DETAILED DESCRIPTION OF THE INVENTION

Various publications are cited throughout the present application. The contents of these publications and contents of documents cited in these publications are herein incorporated herein by reference.

Accordingly, the present invention provides a compound having the structure represented by formula (I), or its stereoisomer, enantiomer, diastereomer, hydrate, or pharmaceutically acceptable salts thereof:

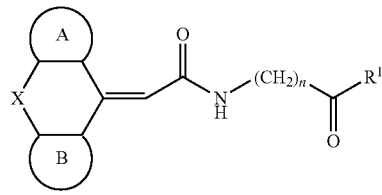

wherein
X is a bond, —CH$_2$CH$_2$—, —CH=CH—, O or S;
Ring A and ring B, fused to the ring containing X, independently of each other represents a benzene ring, which optionally substituted with one or more halogen, nitro, alkyl, alkoxy or amino;
R$^1$ is —NHOH or

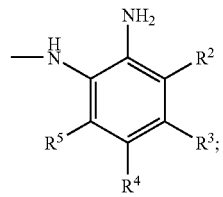

R$^2$, R$^3$, R$^4$ and R$^5$ are independently hydrogen, halo, alkyl, alkoxy or trifluoromethyl;
n is an integer ranging from 1 to 7.

In the above structural formula (I) and throughout the present specification, the following terms have the indicated meaning:

The term "halo" as used herein means fluorine, chlorine, bromine or iodine.

The term "alkyl" as used herein includes methyl, ethyl, n-propyl, iso-propyl, butyl, iso-butyl, sec-butyl, tert-butyl and the like.

The term "alkoxy" as used herein includes methoxy, ethoxy, n-propoxy, isopropoxy, n-butoxy, isobutoxy and the like.

In one embodiment of a compound of formula (I), X is a bond, —CH$_2$CH$_2$—, —CH=CH—, O or S; Ring A and ring B, fused to the ring containing X, independently of each other represents a benzene ring; R$^1$ is —NHOH; and n is an integer ranging from 4 to 7.

In another embodiment, X is a bond, —CH$_2$CH$_2$—, —CH=CH—, O or S; Ring A and ring B, used to the ring containing X, independently of each other represents a benzene ring; R$^1$ is

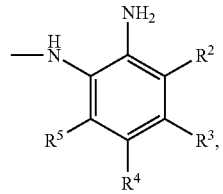

wherein R$^2$, R$^3$, R$^4$ and R$^5$ are independently hydrogen, halo, alkyl, alkoxy or trifluoromethyl; and an integer ranging from 4 to 7.

In another embodiment, is a bond; Ring A and ring B, fused to the ring containing X, independently of each other represents a benzene ring; R$^1$ is —NHOH; and n is an integer ranging from 4 to 7.

In another embodiment, X is a bond; Ring A and ring B, fused to the ring containing X, independently of each other represents a benzene ring; $R^1$ is

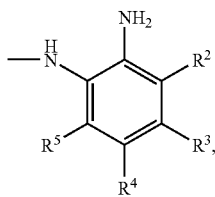

wherein $R^2$, $R^3$, $R^4$ and $R^5$ are independently hydrogen, halo, alkyl, alkoxy or trifluoromethyl; and n is an integer ranging from 4 to 7.

The compounds of this invention are prepared as described below:

(a) Compound 1 is condensed with compound 2 to give compound 3;

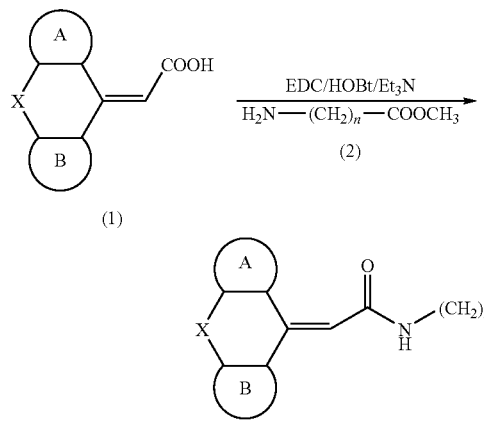

(b) Compound 3 is hydrolyzed to give compound 4;

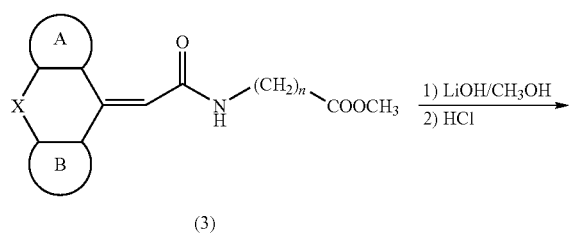

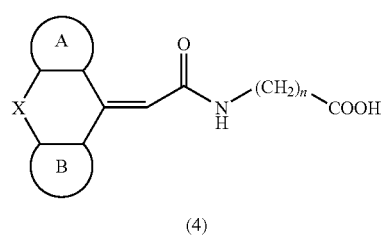

(c) Compound 4 is condensed with hydroxylamine to give compound 5a;

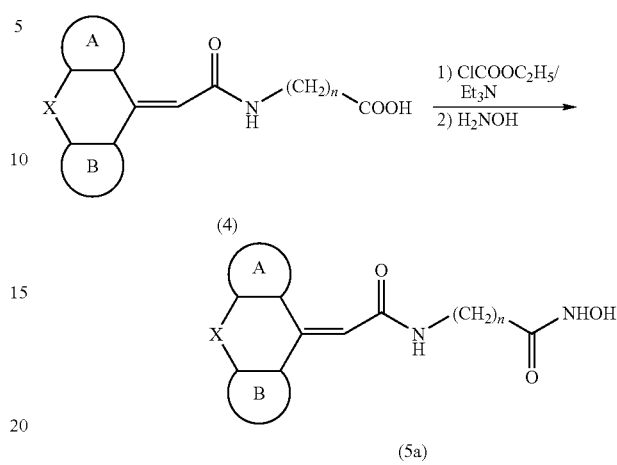

(d) Compound 4 is condensed with compound 6 to give compound 5b.

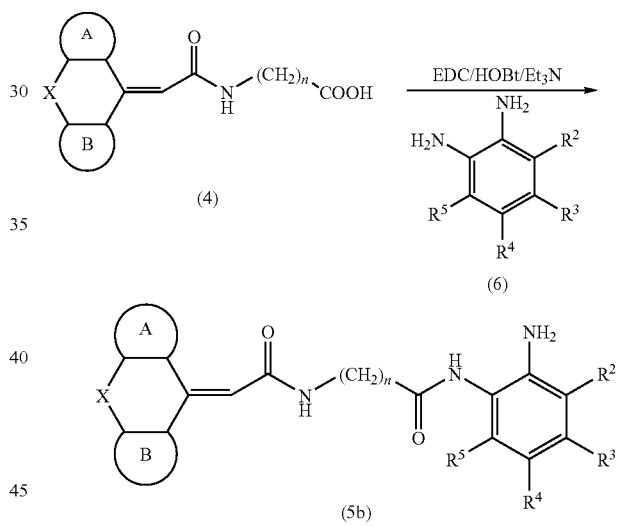

Condensation reactions (a) and (d) are conducted by using a peptide condensing agent such as 1-ethyl-3-(3-dimethylaminopropyl)carbodiimide (EDC), dicyclohexylcarbodiimide (DCC), N,N'-carbonyldiimidazole (CDI), etc. The reaction may be conducted at 0 to 80° C. for 4 to 72 hours. Solvents which may be used are normal solvents such as benzene, toluene, tetrahydrofuran, dioxane, dichloromethane, chloroform, N,N-dimethylformamide, etc. If necessary, a base such as sodium hydroxide, triethylamine and pyridine may be added to the reaction system.

Condensation reaction (c) is conducted by using ClCOOEt as a condensing agent. The reaction may be conducted at 0 to 80° C. for 1 to 24 hours. Solvents which may be used are normal solvents such as benzene, toluene, tetrahydrofuran, dioxane, dichloromethane, chloroform, N,N-dimethylformamide, etc. If necessary, a base such as sodium hydroxide, triethylamine and pyridine may be added to the reaction system.

The hydrolysis reaction (b) is conducted by using a hydrolysis agent such as lithium hydroxide, sodium hydroxide, potassium hydroxide, etc. The reaction may be conducted at 0 to 80° C. for 2 to 72 hours. Solvents which may be used are normal solvents such as water, methanol, ethanol, tetrahydrofuran, dioxane, N,N-dimethylformamide, etc.

The compounds represented by formula (I) and the intermediate (3) and (4) may be purified or isolated by the conventional separation method such as extraction, recrystallization, column chromatography and the like.

This invention also provides a compound having the structure represented by formula (II), or its stereoisomer, enantiomer, diastereomer, hydrate, or pharmaceutically acceptable salts thereof:

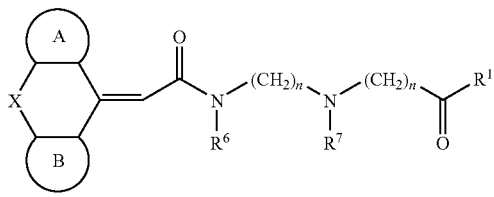

(II)

wherein
X is a bond, —CH2CH2-, —CH═CH—, O or S;
Ring A and ring B, fused to the ring containing X, independently of each other represents a benzene ring, which optionally substituted with one or more halogen, nitro, alkyl, alkoxy or amino;
$R^1$ is —NHOH or

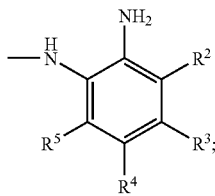

$R^2$, $R^3$, $R^4$ and $R^5$ are independently hydrogen, halo, alkyl, alkoxy or trifluoromethyl;

$R^6$ and $R^7$ are independently hydrogen or alkyl;
m is an integer ranging from 2 to 4;
n is an integer ranging from 1 to 7.

The compounds represented by formula (I) or formula (II) are capable of inhibiting histone deacetylases and are therefore useful in treating diseases associated with abnormal histone deacetylase activities. In particular, they are highly effective against Rubinstein-Taybi syndrome, fragile X syndrome, leukemia, cancer and various neurological and neurodegenerative disorders. Thus, the invention also provides a method of treating such diseases in a mammals, including man and animals, in need of such treatment, comprising administering a compound of formula (I) or (II) or a pharmaceutically acceptable salt thereof.

The compounds represented by formula (I) or formula (II) useful as a drug may be used in the form of a general pharmaceutical composition. The pharmaceutical composition may be in the forms normally employed, such as tablets, capsules, powders, syrups, solutions, suspensions, aerosols, and the like, may contain flavourants, sweeteners etc. in suitable solids or liquid carriers or diluents, or in suitable sterile media to form injectable solutions or suspensions. Such composition typically contains from 0.5 to 70%, preferably 1 to 20% by weight of active compound, the remainder of the composition being pharmaceutically acceptable carriers, diluents or solvents or salt solutions.

The compounds represented by formula (I) or formula (II) are clinically administered to mammals, including man and animals, via oral, nasal, transdermal, pulmonary, or parenteral routes. Administration by the oral route is preferred, being more convenient and avoiding the possible pain and irritation of injection. By either route, the dosage is in the range of about 0.0001 to 200 mg/kg body weight per day administered singly or as a divided dose. However, the optimal dosage for the individual subject being treated will be determined by the person responsible for treatment, generally smaller dose being administered initially and thereafter increments made to determine the most suitable dosage.

Representative compounds of the present invention are shown in Table 1 below. The compound numbers correspond to the "Example numbers" in the Examples section. That is, the synthesis of compound 1 as shown in the Table 1 is described in "Example 1" and the synthesis of compound 52 as shown in the Table 1 is described in "Example 52". The compounds presented in the Table 1 are exemplary only and are not to be construed as limiting the scope of this invention in any manner.

TABLE 1

| Example | Structure | Name |
| --- | --- | --- |
| 2 | 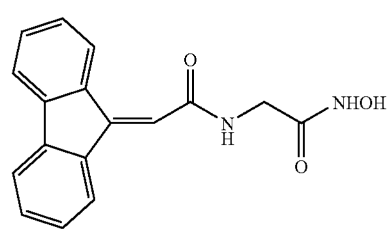 | 2-(2-(9H-fluoren-9-ylidene)-acetamido)-N-hydroxyacetamide |

TABLE 1-continued

| Example | Structure | Name |
|---|---|---|
| 4 | 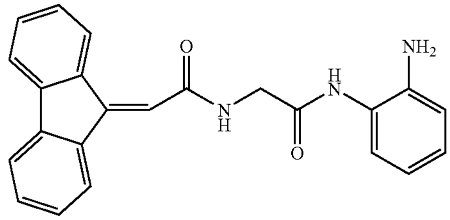 | 2-(2-(9H-fluoren-9-ylidene)-acetamido)-N-(2-aminophenyl)-acetamide |
| 7 | 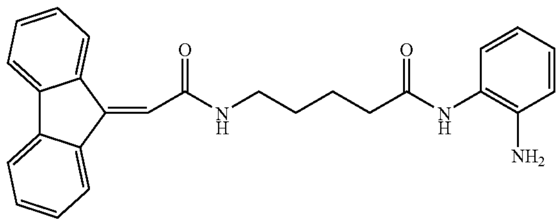 | 5-(2-(9H-fluoren-9-ylidene)-acetamido)-N-(2-aminophenyl)-pentanamide |
| 8 | 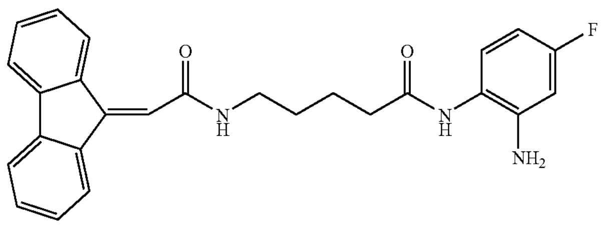 | 5-(2-(9H-fluoren-9-ylidene)-acetamido)-N-(2-amino-4-fluoro-phenyl)pentanamide |
| 11 | 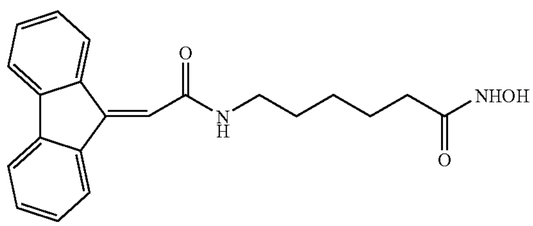 | 6-(2-(9H-fluoren-9-ylidene)-acetamido)-N-hydroxy-hexanamide |
| 12 | 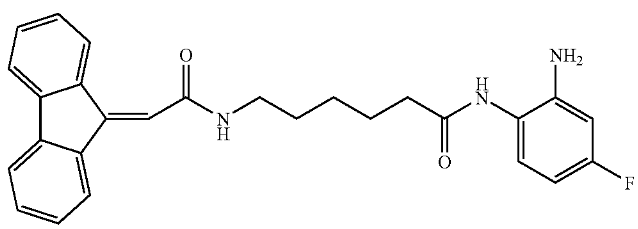 | 6-(2-(9H-fluoren-9-ylidene)-acetamido)-N-(2-amino-4-fluoro-phenyl)hexanamide |
| 13 | 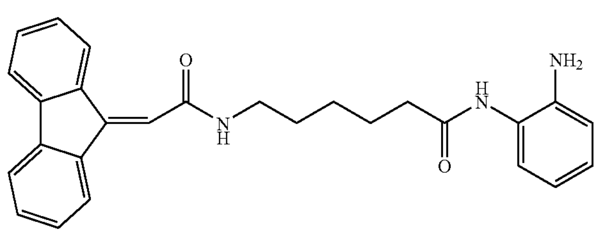 | 6-(2-(9H-fluoren-9-ylidene)-acetamido)-N-(2-aminophenyl)-hexanamide |
| 14 | 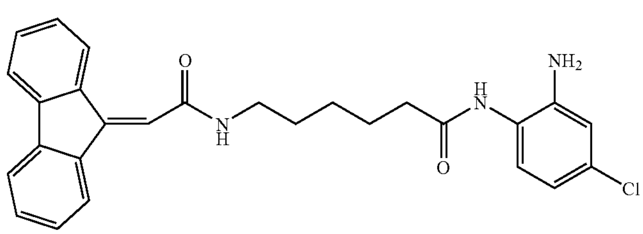 | 6-(2-(9H-fluoren-9-ylidene)-acetamido)-N-(2-amino-4-chloro-phenyl)hexanamide |

TABLE 1-continued

| Example | Structure | Name |
|---|---|---|
| 15 | 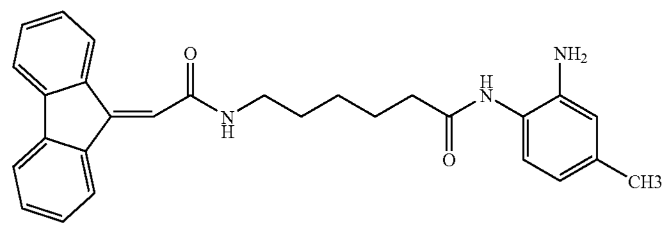 | 6-(2-(9H-fluoren-9-ylidene)-acetamido)-N-(2-amino-4-methyl-phenyl)hexanamide |
| 16 | 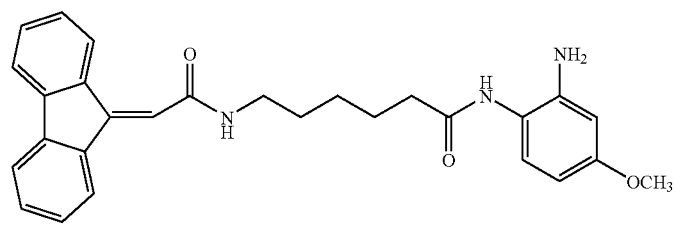 | 6-(2-(9H-fluoren-9-ylidene)-acetamido)-N-(2-amino-4-methoxyphenyl)hexanamide |
| 17 | 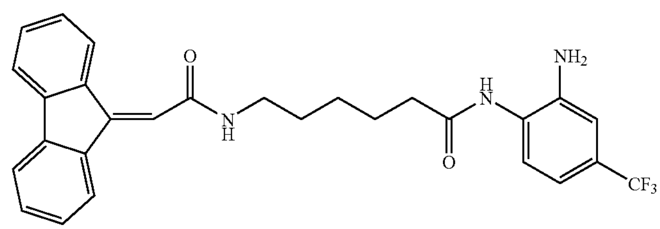 | 6-(2-(9H-fluoren-9-ylidene)-acetamido)-N-(2-amino-4-trifluoromethylphenyl)-hexanamide |
| 18 | 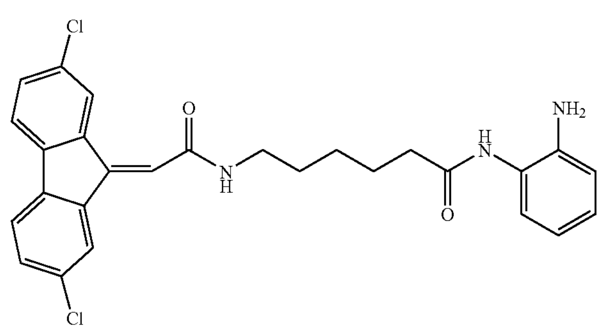 | 6-(2-(2,7-dichloro-9H-fluoren-9-ylidene)acetamido)-N-(2-amino-phenyl)hexanamid |
| 19 | 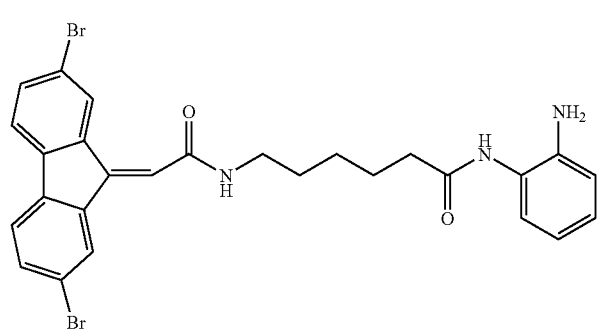 | 6-(2-(2,7-dibromo-9 H-fluoren-9-ylidene)acetamido)-N-(2-amino-phenyl)hexanamid |

TABLE 1-continued

| Example | Structure | Name |
|---|---|---|
| 20 | 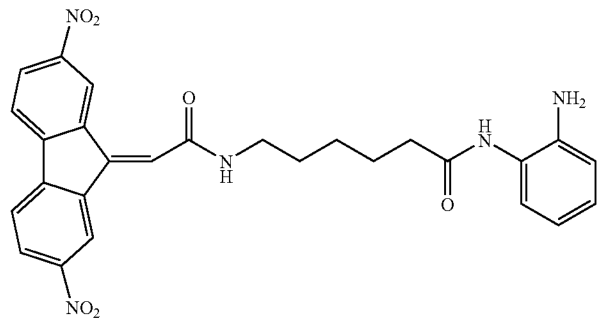 | 6-(2-(2,7-dinitro-9H-fluoren-9-ylidene)acetamido)-N-(2-aminophenyl)hexanamid |
| 21 | 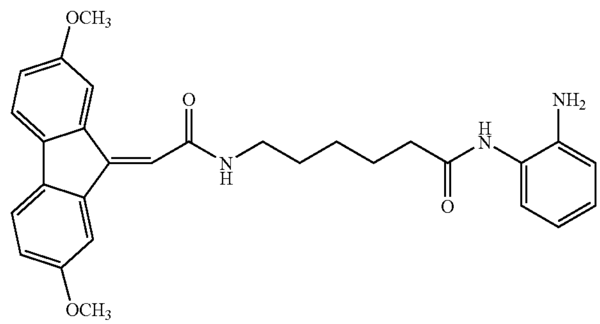 | 6-(2-(2,7-dimethoxy-9H-fluoren-9-ylidene)acetamido)-N-(2-aminophenyl)hexanamid |
| 22 | 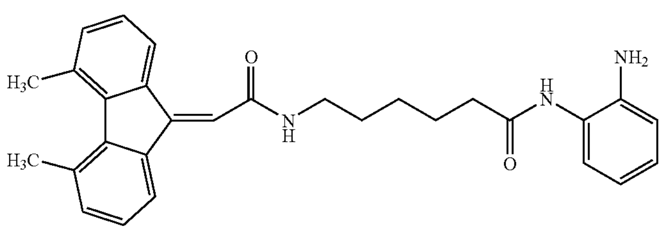 | 6-(2-(4,5-dimethyl-9H-fluoren-9-ylidene)acetamido)-N-(2-aminophenyl)hexanamid |
| 23 | 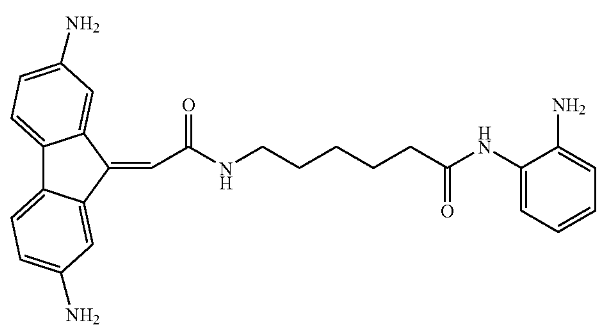 | 6-(2-(2,7-diamino-9H-fluoren-9-ylidene)acetamido)-N-(2-aminophenyl)hexanamid |
| 26 | 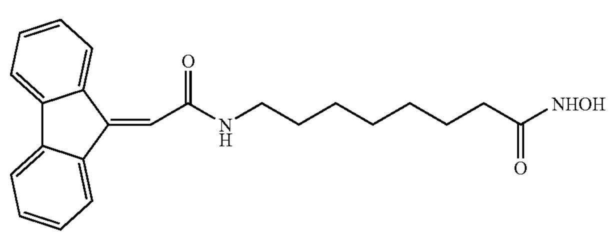 | 8-(2-(9H-fluoren-9-ylidene)-acetamido)-N-hydroxy-octanamide |

TABLE 1-continued

| Example | Structure | Name |
|---|---|---|
| 27 | 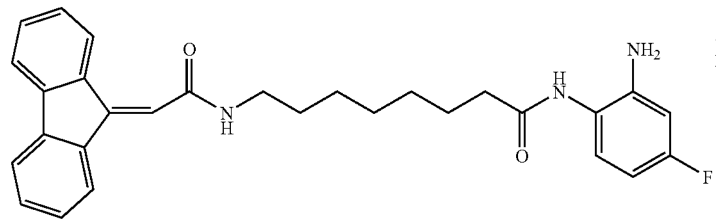 | 8-(2-(9H-fluoren-9-ylidene)-acetamido)-N-(2-amino-4-fluorophenyl)octanamide |
| 28 | 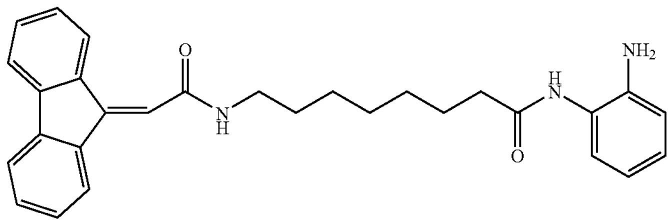 | 8-(2-(9H-fluoren-9-ylidene)-acetamido)-N-hydroxy-octanamide |
| 31 | 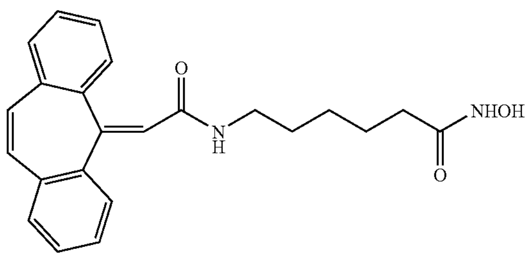 | 6-(2-(5H-dibenzocyclohepten-5-ylidene)acetamido)-N-hydroxyhexanamide |
| 34 | 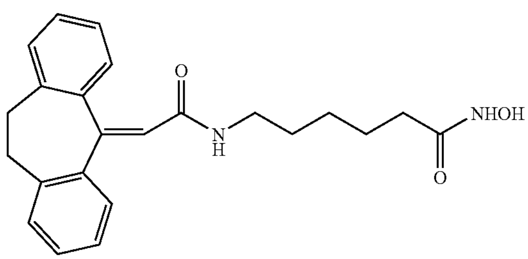 | 6-(2-(10,11-dihydro-5H-dibenzocyclohepten-5-ylidene)acetamido)-N-hydroxyhexanamide |
| 37 | 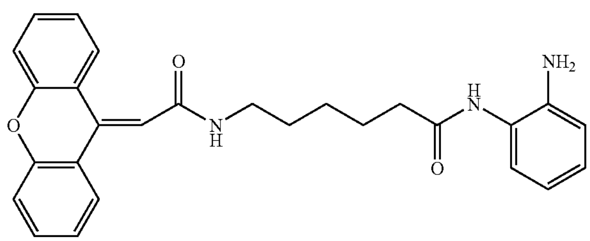 | 6-(2-(9H-xanthen-9-ylidene)-acetamido)-N-(2-aminophenyl)-hexanamide |
| 40 | 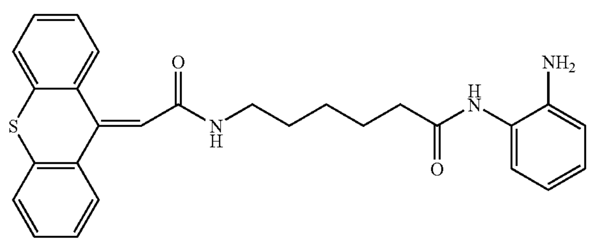 | 6-(2-(9H-thioxanthen-9-ylidene)-acetamido)-N-(2-aminophenyl)-hexanamide |

Further, all parts and percentages in the examples, as well as in the remainder of the specification, are by weight unless otherwise specified. Any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result.

Example 1

Preparation of 2-(2-(9H-fluoren-9-ylidene)acetamido)acetic acid methyl ester

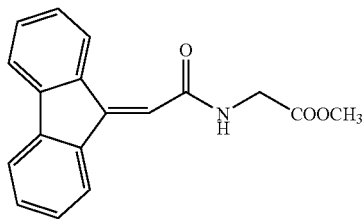

2-(9H-fluoren-9-ylidene)acetic acid (222 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and glycine methyl ester hydrochloride (151.8 mg, 1.2 mmol) were added. The mixture was stirred for 24 hours at room temperature. The mixture was diluted with 400 mL of brine. The solids were collected by vacuum filtration, washed with water and dried under vacuum to give the title compound (256 mg, 88% yield) as a white solid. LC-MS (m/z) 294 (M+1).

Example 2

Preparation of 2-(2-(9H-fluoren-9-ylidene)acetamido)acetic acid

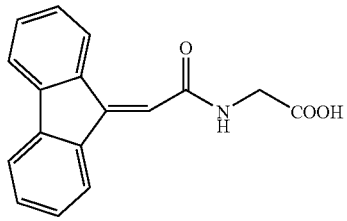

2-(2-(9H-fluoren-9-ylidene)acetamido)acetic acid methyl ester (293 mg, 1 mmol) and 300 ml of $CH_3OH$ were stirred at room temperature while 25 ml of 4 N solution of LiOH in $H_2O$ was added. The mixture was stirred for 5 hours at room temperature. The mixture is neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (259 mg, 93% yield) as a white solid. LC-MS (m/z) 280 (M+1).

Example 3

Preparation of 2-(2-(9H-fluoren-9-ylidene)acetamido)-N-hydroxyacetamide

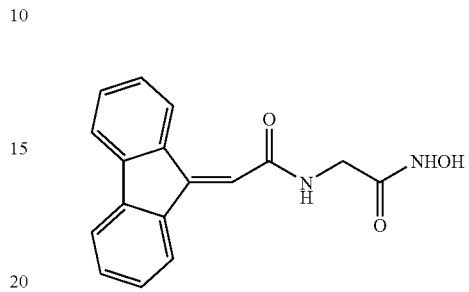

2-(2-(9H-fluoren-9-ylidene)acetamido)acetic acid (279 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (132 mg, 45%) as a yellow solid. LC-MS (m/z) 295 (M+1).

Example 4

Preparation of 2-(2-(9H-fluoren-9-ylidene)acetamido)-N-(2-aminophenyl)acetamide

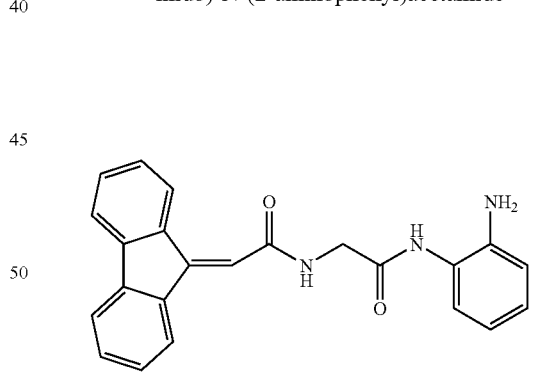

2-(2-(9H-fluoren-9-ylidene)acetamido)acetic acid (279 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried

Example 5

Preparation of 5-(2-(9H-fluoren-9-ylidene)acetamido)pentanoic acid methyl ester

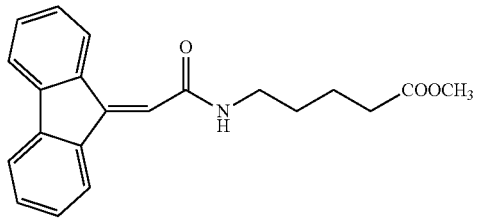

2-(9H-fluoren-9-ylidene)acetic acid (222 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and 5-aminovaleric acid methyl ester hydrochloride (202 mg, 1.2 mmol) were added. The mixture was stirred for 24 hours at room temperature. The mixture was diluted with 400 mL of brine. The solids were collected by vacuum filtration, washed with water and dried under vacuum to give the title compound (278 mg, 68% yield) as a white solid. LC-MS (m/z) 336 (M+1).

Example 6

Preparation of 5-(2-(9H-fluoren-9-ylidene)acetamido)pentanoic acid

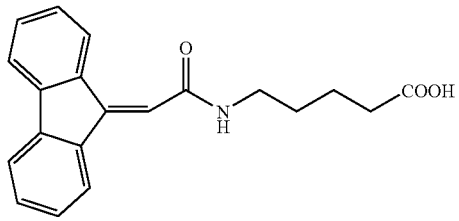

5-(2-(9H-fluoren-9-ylidene)acetamido)pentanoic acid methyl ester (335 mg, 1 mmol) and 300 ml of $CH_3OH$ were stirred at room temperature while 25 ml of 4 N solution of LiOH in $H_2O$ was added. The mixture was stirred for 24 hours at room temperature. The mixture was neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (295 mg, 80% yield) as a brown solid. LC-MS (m/z) 370 (M+1).

Example 7

Preparation of 5-(2-(9H-fluoren-9-ylidene)acetamido)-N-(2-aminophenyl)pentanamide

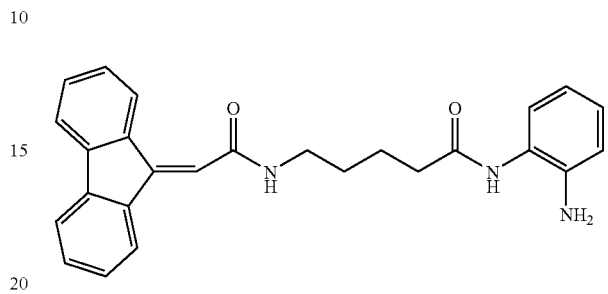

5-(2-(9H-fluoren-9-ylidene)acetamido)pentanoic acid (321 mg, 1 mmol), and 8 ml of DMF were stirred at room temperature while 1-Ethyl-3-(3-dimethylaminopropyl)carbodiimide hydrochloride (394 mg, 2 mmol), hydroxy-benzo-triazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (292 mg, 71% yield) as a brown solid. LC-MS (m/z) 412 (M+1).

Example 8

Preparation of 5-(2-(9H-fluoren-9-ylidene)acetamido)-N-(2-amino-4-fluorophenyl)pentanamide

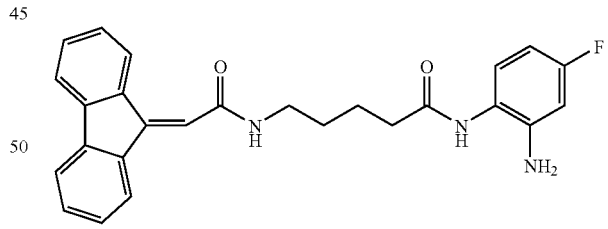

5-(2-(9H-fluoren-9-ylidene)acetamido)pentanoic acid (321 mg, 1 mmol), and 8 ml of DMF were stirred at room temperature while 1-Ethyl-3-(3-dimethylaminopropyl)carbodiimide hydrochloride (394 mg, 2 mmol), hydroxy-benzo-triazole (162 mg, 1.2 mmol), triethylamine (404 mg, 4 mmol) and 4-fluoro-9-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (369 mg, 86% yield) as a brown solid. LC-MS (m/z) 430 (M+1).

Example 9

Preparation of 6-(2-(9H-fluoren-9-ylidene)acetamido)hexanoic acid methyl ester

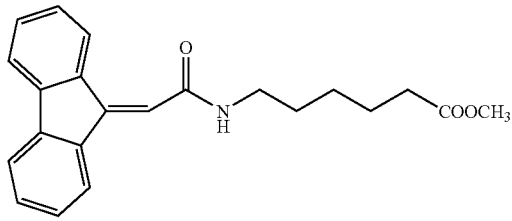

2-(9H-fluoren-9-ylidene)acetic acid (222 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and 6-aminocaproic acid methyl ester hydrochloride (219 mg, 1.2 mmol) were added. The mixture was stirred for 24 hours at room temperature. The mixture was diluted with 400 mL of brine. The solids were collected by vacuum filtration, washed with water and dried under vacuum to give the title compound (317 mg, 91% yield) as a white solid. LC-MS (m/z) 350 (M+1).

Example 10

Preparation of 6-(2-(9H-fluoren-9-ylidene)acetamido)hexanoic acid

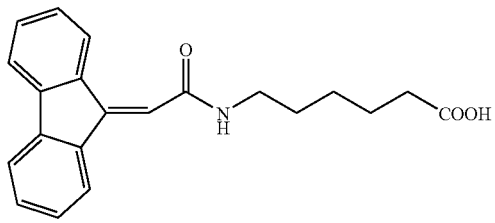

6-(2-(9H-fluoren-9-ylidene)acetamido)hexanoic acid methyl ester (349 mg, 1 mmol) and 300 ml of CH$_3$OH were stirred at room temperature while 25 ml of 4 N solution of LiOH in H$_2$O was added. The mixture was stirred for 24 hours at room temperature. The mixture was neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (281 mg, 84% yield) as a white solid. $^1$H NMR (DMSO-d$_6$) δ1.30 (m, 2H, CH$_2$), 1.51 (m, 4H, 2×CH$_2$), 2.18 (t, J=8.0 Hz, 2H, CH$_2$CO), 3.23 (m, 2H, NCH$_2$), 7.08 (s, 1H, =CH—CO), 7.34 (m, 2H, Ar—H), 7.41 (t, J=8.0 Hz, 2H, Ar—H), 7.76 (d, J=8.0 Hz, 1H, Ar—H), 7.81 (m, 2H, Ar—H), 8.53 (t, J=4.0 Hz, 1H, CONH), 8.68 (d, J=8.0 Hz, 1H, Ar—H). LC-MS (m/z) 336 (M+1).

Example 11

Preparation of 6-(2-(9H-fluoren-9-ylidene)acetamido)-N-hydroxyhexanamide

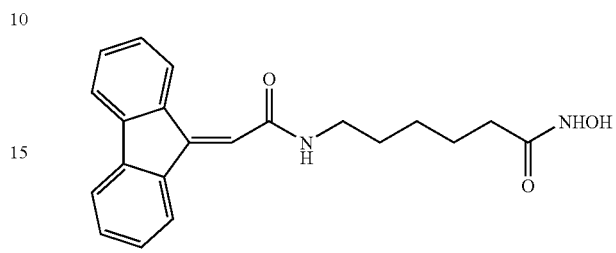

6-(2-(9H-fluoren-9-ylidene)acetamido)hexanoic acid (335 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (147 mg, 42%) as a yellow solid. $^1$H NMR (DMSO-d$_6$) δ1.19 (m, 2H, CH$_2$), 1.30 (m, 2H, CH$_2$), 1.48 (m, 2H, CH$_2$), 1.92 (t, J=8.0 Hz, 2H, CH$_2$CO), 3.24 (m, 2H, NCH$_2$), 7.08 (s, 1H, =CH—CO), 7.28 (m, 2H, Ar—H), 7.41 (m, 2H, Ar—H), 7.76 (m, 1H, Ar—H), 7.81 (m, 2H, Ar—H), 8.53 (t, J=4.0 Hz, 1H, CONH), 8.67 (d, J=8.0 Hz, 1H, Ar—H), 10.32 (s, 1H, NH—O). LC-MS (m/z) 351 (M+1).

Example 12

Preparation of 6-(2-(9H-fluoren-9-ylidene)acetamido)-N-(2-amino-4-fluorophenyl)hexanamide

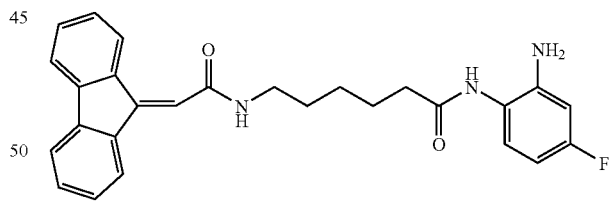

6-(2-(9H-fluoren-9-ylidene)acetamido)hexanoic acid (335 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (350 mg, 79% yield) as a brown solid. $^1$H NMR (DMSO-d$_6$) δ1.39 (m, 2H, CH$_2$), 1.57 (m, 2H, CH$_2$), 1.63 (m, 2H, CH$_2$), 2.31 (t, J=8.0 Hz, 2H, CH$_2$CO), 3.26 (m, 2H, NCH$_2$), 5.13 (s, 2H, benzene-NH$_2$), 6.26 (t, J=8.0 Hz, 1H, Ar—H), 6.46 (d, J=8.0

Hz, 1H, Ar—H), 7.08 (s, 1H, =CH—CO and Ar—H), 7.33 (m, 2H, Ar—H), 7.40 (m, 2H, Ar—H), 7.76 (d, J=8.0 Hz, 1H, Ar—H), 7.82 (m, 2H, Ar—H), 8.53 (t, J=4.0 Hz, 1H, CONH), 8.69 (d, J=8.0 Hz, 1H, Ar—H), 9.03 (s, 1H, benzene-NH). LC-MS (m/z) 444 (M+1).

Example 13

Preparation of 6-(2-(9H-fluoren-9-ylidene)acetamido)-N-(2-aminophenyl)hexanamide

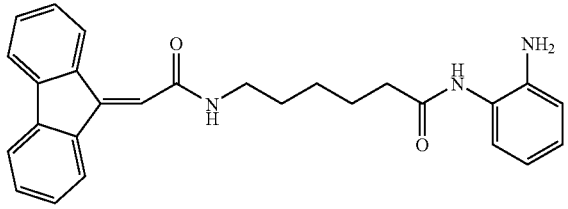

6-(2-(9H-fluoren-9-ylidene)acetamido)hexanoic acid (335 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (353 mg, 83% yield) as a brown solid. $^1$H NMR (DMSO-d$_6$) δ1.37 (m, 2H, CH$_2$), 1.55 (m, 2H, CH$_2$), 1.63 (m, 2H, CH$_2$), 2.32 (t, J=8.0 Hz, 2H, CH$_2$CO), 3.25 (m, 2H, NCH$_2$), 4.81 (s, 2H, benzene-NH$_2$), 6.51 (t, J=8.0 Hz, 1H, Ar—H), 6.69 (d, J=8.0 Hz, 1H, Ar—H), 6.87 (t, J=8.0 Hz, 1H, Ar—H), 7.08 (s, 1H, =CH—CO), 7.13 (d, J=8.0 Hz, 1H, Ar—H), 7.31 (m, 2H, Ar—H), 7.41 (t, J=8.0 Hz, 2H, Ar—H), 7.76 (d, J=8.0 Hz, 1H, Ar—H), 7.81 (m, 2H, Ar—H), 8.53 (t, J=4.0 Hz, 1H, CONH), 8.69 (d, J=8.0 Hz, 1H, Ar—H), 9.09 (s, 1H, benzene-NH). LC-MS (m/z) 426 (M+1).

Example 14

Preparation of 6-(2-(9H-fluoren-9-ylidene)acetamido)-N-(2-amino-4-chlorophenyl)hexanamide

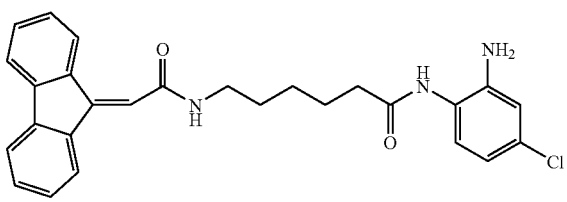

6-(2-(9H-fluoren-9-ylidene)acetamido)hexanoic acid (335 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-chloro-o-phenylenediamine (171 mg, 1.2 mmol) were added. The mixture was stirred for 24 hours at room temperature. The mixture was diluted with 400 mL of brine. The solids were collected by vacuum filtration, washed with water and dried under vacuum to give the title compound (353 mg, 77% yield) as a brown solid. $^1$H NMR (DMSO-d$_6$) δ1.38 (m, 2H, CH$_2$), 1.59 (m, 2H, CH$_2$), 1.63 (m, 2H, CH$_2$), 2.34 (t, J=8.0 Hz, 2H, CH$_2$CO), 3.26 (m, 2H, NCH$_2$), 5.18 (s, 2H, benzene-NH$_2$), 6.49 (d, J=8.0 Hz, 1H, Ar—H), 6.72 (s, 1H, Ar—H), 7.10 (s, 1H, =CH—CO), 7.19 (d, J=8.0 Hz, 1H, Ar—H), 7.33 (m, 2H, Ar—H), 7.40 (m, 2H, Ar—H), 7.76 (d, J=8.0 Hz, 1H, Ar—H), 7.82 (m, 2H, Ar—H), 8.57 (t, J=4.0 Hz, 1H, CONH), 8.71 (d, J=8.0 Hz, 1H, Ar—H), 9.17 (s, 1H, benzene-NH). LC-MS (m/z) 459 (M+1).

Example 15

Preparation of 6-(2-(9H-fluoren-9-ylidene)acetamido)-N-(2-amino-4-methylphenyl)hexanamide

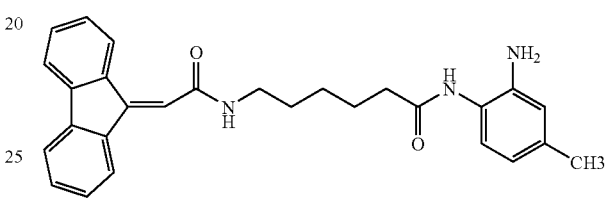

6-(2-(9H-fluoren-9-ylidene)acetamido)hexanoic acid (335 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-methyl-o-phenylenediamine (146 mg, 1.2 mmol) were added. The mixture was stirred for 24 hours at room temperature. The mixture was diluted with 400 mL of brine. The solids were collected by vacuum filtration, washed with water and dried under vacuum to give the title compound (369 mg, 84% yield) as a brown solid. $^1$H NMR (DMSO-d$_6$) δ1.39 (m, 2H, CH$_2$), 1.57 (m, 2H, CH$_2$), 1.63 (m, 2H, CH$_2$), 2.11 (s, 3H, CH$_3$), 2.31 (t, J=8.0 Hz, 2H, CH$_2$CO), 3.27 (m, 2H, NCH$_2$), 4.72 (s, 2H, benzene-NH$_2$), 6.31 (d, J=8.0 Hz, 1H, Ar—H), 6.61 (s, 1H, Ar—H), 6.99 (d, J=8.0 Hz, 1H, Ar—H), 7.08 (s, 1H, =CH—CO), 7.33 (m, 2H, Ar—H), 7.40 (m, 2H, Ar—H), 7.76 (d, J=8.0 Hz, 1H, Ar—H), 7.82 (m, 2H, Ar—H), 8.53 (t, J=4.0 Hz, 1H, CONH), 8.69 (d, J=8.0 Hz, 1H, Ar—H), 9.08 (s, 1H, benzene-NH). LC-MS (m/z) 440 (M+1).

Example 16

Preparation of 6-(2-(9H-fluoren-9-ylidene)acetamido)-N-(2-amino-4-methoxyphenyl)hexanamide

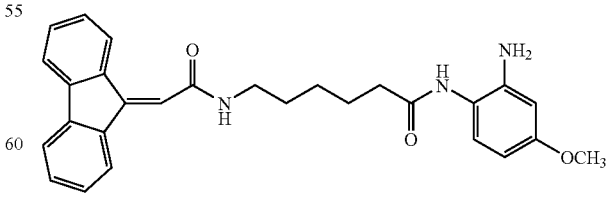

6-(2-(9H-fluoren-9-ylidene)acetamido)hexanoic acid (335 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-methoxy-o-phenylenediamine (166 mg, 1.2 mmol) were added. The mixture was stirred for 24 hours at room temperature. The mixture was diluted with 400 mL of brine. The solids were collected by vacuum filtration, washed with water and dried under vacuum to give the title compound (332 mg, 73% yield) as a brown solid. $^1$H NMR (DMSO-$d_6$) δ1.39 (m, 2H, CH$_2$), 1.55 (m, 2H, CH$_2$), 1.62 (m, 2H, CH$_2$), 2.29 (t, J=8.0 Hz, 2H, CH$_2$CO), 3.27 (m, 2H, NCH$_2$), 3.62 (s, 3H, OCH$_3$), 4.84 (s, 2H, benzene-NH$_2$), 6.08 (d, J=8.0 Hz, 1H, Ar—H), 6.28 (s, 1H, Ar—H), 6.95 (d, J=8.0 Hz, 1H, Ar—H), 7.10 (s, 1H, =CH—CO), 7.33 (m, 2H, Ar—H), 7.40 (m, 2H, Ar—H), 7.76 (d, J=8.0 Hz, 1H, Ar—H), 7.82 (m, 2H, Ar—H), 8.58 (t, J=4.0 Hz, 1H, CONH), 8.72 (d, J=8.0 Hz, 1H, Ar—H), 9.02 (s, 1H, benzene-NH). LC-MS (m/z) 456 (M+1).

Example 17

Preparation of 6-(2-(9H-fluoren-9-ylidene)acetamido)-N-(2-amino-4-trifluoromethylphenyl)hexanamide

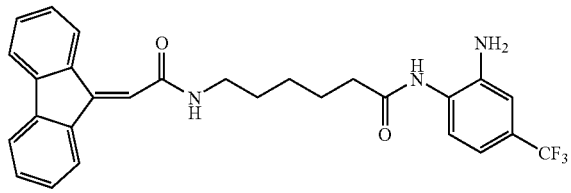

6-(2-(9H-fluoren-9-ylidene)acetamido)hexanoic acid (335 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and 4-trifluoromethyl-o-phenylenediamine (211 mg, 1.2 mmol) were added. The mixture was stirred for 24 hours at room temperature. The mixture was diluted with 400 mL of brine. The solids were collected by vacuum filtration, washed with water and dried under vacuum to give the title compound (286 mg, 58% yield) as a brown solid. LC-MS (m/z) 494 (M+1).

Example 18

Preparation of 6-(2-(2,7-dichloro-9H-fluoren-9-ylidene)acetamido)-N-(2-aminophenyl)hexanamide

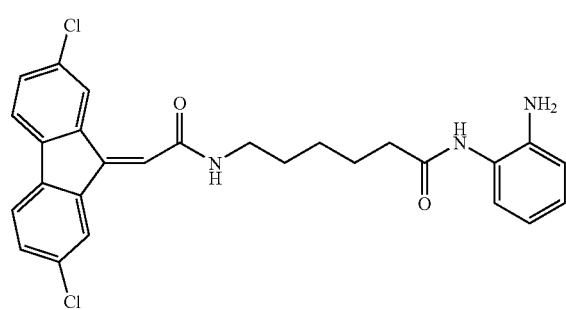

6-(2-(2,7-dichloro-9H-fluoren-9-ylidene)acetamido)hexanoic acid (403 mg, 1 mmol), and 8 ml of DMF were stirred at room temperature while 1-Ethyl-3-(3-dimethylaminopropyl)-carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (351 mg, 71% yield) as a brown solid. LC-MS (m/z) 494 (M+1).

Example 19

Preparation of 6-(2-(2,7-dibromo-9H-fluoren-9-ylidene)acetamido)-N-(2-aminophenyl)hexanamide

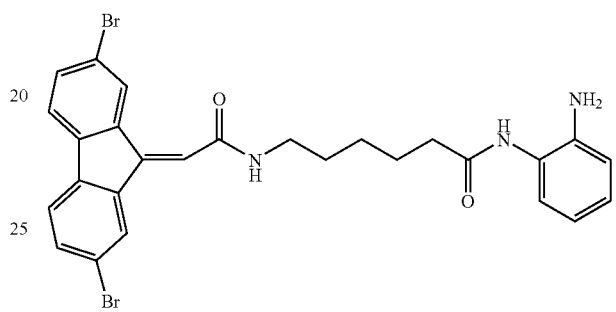

6-(2-(2,7-dibromo-9H-fluoren-9-ylidene)acetamido)hexanoic acid (493 mg, 1 mmol), and 8 ml of DMF were stirred at room temperature while 1-Ethyl-3-(3-dimethylaminopropyl)-carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (437 mg, 76% yield) as a brown solid. LC-MS (m/z) 584 (M+1).

Example 20

Preparation of 6-(2-(2,7-dinitro-9H-fluoren-9-ylidene)acetamido)-N-(2-aminophenyl)hexanamid

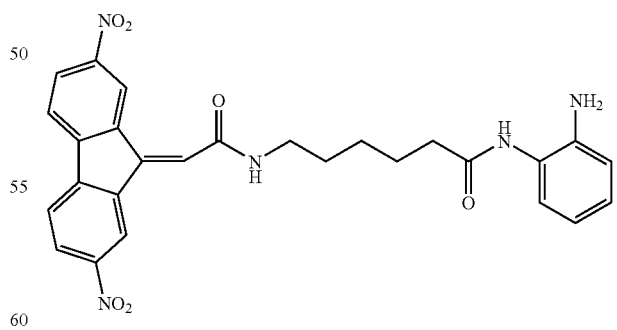

6-(2-(2,7-dinitro-9H-fluoren-9-ylidene)acetamido)hexanoic acid (425 mg, 1 mmol), and 8 ml of DMF were stirred at room temperature while 1-Ethyl-3-(3-dimethylaminopropyl)-carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol)

Example 21

Preparation of 6-(2-(2,7-dimethoxy-9H-fluoren-9-ylidene)acetamido)-N-(2-aminophenyl)hexanamid

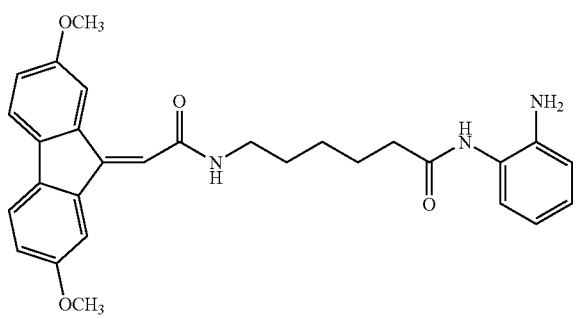

6-(2-(2,7-dimethoxy-9H-fluoren-9-ylidene)acetamido) hexanoic acid (395 mg, 1 mmol), and 8 ml of DMF were stirred at room temperature while 1-Ethyl-3-(3-dimethylaminopropyl)-carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (373 mg, 77% yield) as a brown solid. LC-MS (m/z) 486 (M+1).

Example 22

Preparation of 6-(2-(4,5-dimethyl-9H-fluoren-9-ylidene)acetamido)-N-(2-aminophenyl)hexanamide

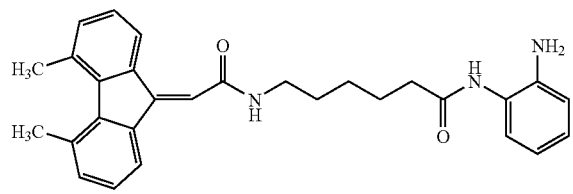

6-(2-(4,5-dimethyl-9H-fluoren-9-ylidene)acetamido)hexanoic acid (363 mg, 1 mmol), and 8 ml of DMF were stirred at room temperature while 1-Ethyl-3-(3-dimethylaminopropyl)-carbodiimide hydrochloride (394 mg, 2 mmol), hydroxyl-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (326 mg, 72% yield) as a brown solid. LC-MS (m/z) 454 (M+1).

Example 23

Preparation of 6-(2-(2,7-diamino-9H-fluoren-9-ylidene)acetamido)-N-(2-aminophenyl)hexanamide

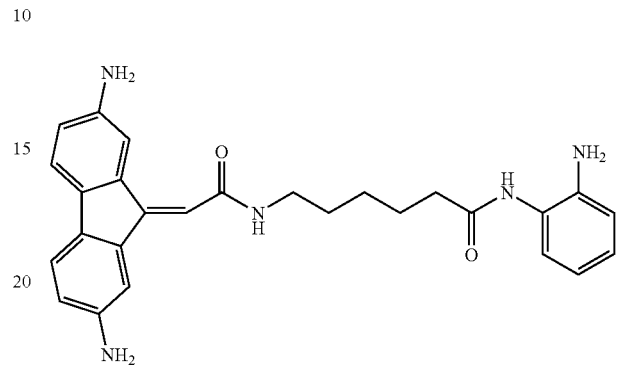

To a solution of 6-(2-(2,7-dinitro-9H-fluoren-9-ylidene)acetamido)-N-(2-aminophenyl)-hexanamide (515 mg, 1 mmol) in methanol (20 ml) was added 5% palladium on charcoal (0.50 g). Then the mixture was stirred under an atmosphere of hydrogen at room temperature until hydrogen uptake ceased. The solution was filtered through celite, and the filtrate was evaporated under vacuum to give the title compound (437 mg, 96% yield) as a white solid. LC-MS (m/z) 456 (M+1).

Example 24

Preparation of 8-(2-(9H-fluoren-9-ylidene)acetamido)octanoic acid methyl ester

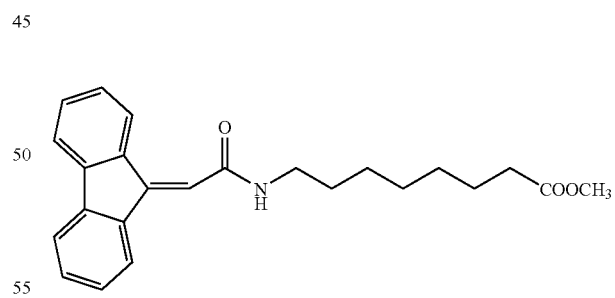

2-(9H-fluoren-9-ylidene)acetic acid (222 mg, 1 mmol) and 8 ml of DMF were stirred at room temperature while 1-Ethyl-3-(3-dimethylaminopropyl)carbodiimide hydrochloride (394 mg, 2 mmol), hydroxyl-benzotriazole (162 mg, 1.2 mmol), triethylamine (404 mg, 4 mmol) and 8-aminocaprylic acid methyl ester hydrochloride (251 mg, 1.2 mmol) were added. The mixture was stirred for 24 hours at room temperature. The mixture was diluted with 400 mL of brine. The solids were collected by vacuum filtration, washed with water and dried under vacuum to give the title compound (328 mg, 87% yield) as a white solid. LC-MS (m/z) 378 (M+1).

Example 25

Preparation of 8-(2-(9H-fluoren-9-ylidene)acetamido)octanoic acid

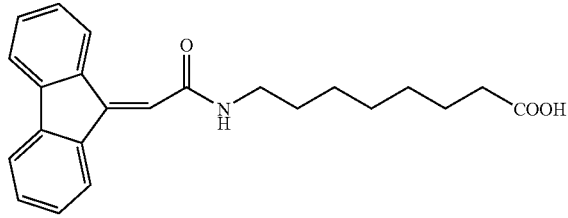

8-(2-(9H-fluoren-9-ylidene)acetamido)octanoic acid methyl ester (377 mg, 1 mmol) and 300 ml of $CH_3OH$ were stirred at room temperature while 25 ml of 4 N solution of LiOH in $H_2O$ was added. The mixture was stirred for 24 hours at room temperature. The mixture was neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (345 mg, 95% yield) as a white solid. $^1$H NMR (DMSO-$d_6$) δ1.23 (m, 2H, $CH_2$), 1.45 (m, 6H, 3×$CH_2$), 1.49 (m, 2H, $CH_2$), 2.18 (t, J=8.0 Hz, 2H, $CH_2CO$), 3.23 (m, 2H, $NCH_2$), 7.08 (s, 1H, =CH—CO), 7.34 (m, 2H, Ar—H), 7.41 (t, J=8.0 Hz, 2H, Ar—H), 7.76 (d, J=8.0 Hz, 1H, Ar—H), 7.81 (m, 2H, Ar—H), 8.50 (t, J=4.0 Hz, 1H, CONH), 8.67 (d, J=8.0 Hz, 1H, Ar—H). LC-MS (m/z) 364 (M+1).

Example 26

Preparation of 8-(2-(9H-fluoren-9-ylidene)acetamido)-N-hydroxyoctanamide

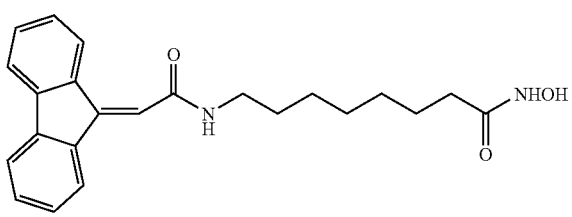

8-(2-(9H-fluoren-9-ylidene)acetamido)octanoic acid (363 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (166 mg, 44%) as a yellow solid. LC-MS (m/z) 379 (M+1).

Example 27

Preparation of 8-(2-(9H-fluoren-9-ylidene)acetamido)-N-(2-amino-4-fluorophenyl)octanamide

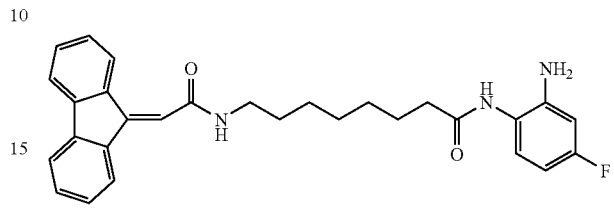

8-(2-(9H-fluoren-9-ylidene)acetamido)octanoic acid (363 mg, 1 mmol), and 8 ml of DMF were stirred at room temperature while 1-Ethyl-3-(3-dimethylaminopropyl)carbodiimide hydrochloride (394 mg, 2 mmol), hydroxyl-benzotriazole (162 mg, 1.2 mmol), triethylamine (404 mg, 4 mmol) and 4-fluoro-o-phenylenediamine (151 mg, 1.2 mmol) were added. The mixture was stirred for 24 hours at room temperature. The mixture was diluted with 400 mL of brine. The solids were collected by vacuum filtration, washed with water and dried under vacuum to give the title compound (330 mg, 70% yield) as a brown solid. $^1$H NMR (DMSO-$d_6$) δ1.33 (m, 6H, 3×$CH_2$), 1.52 (m, 2H, $CH_2$), 1.58 (m, 2H, $CH_2$), 2.29 (t, J=8.0 Hz, 2H, $CH_2CO$), 3.24 (m, 2H, $NCH_2$), 5.12 (s, 2H, benzene-$NH_2$), 6.28 (t, J=8.0 Hz, 1H, Ar—H), 6.46 (d, J=8.0 Hz, 1H, Ar—H), 7.08 (s, 1H, =CH—CO and Ar—H), 7.33 (m, 2H, Ar—H), 7.41 (m, 2H, Ar—H), 7.76 (d, J=8.0 Hz, 1H, Ar—H), 7.82 (m, 2H, Ar—H), 8.52 (t, J=4.0 Hz, 1H, CONH), 8.67 (d, J=8.0 Hz, 1H, Ar—H), 9.02 (s, 1H, benzene-NH). LC-MS (m/z) 472 (M+1).

Example 28

Preparation of 8-(2-(9H-fluoren-9-ylidene)acetamido)-N-(2-aminophenyl)octanamide

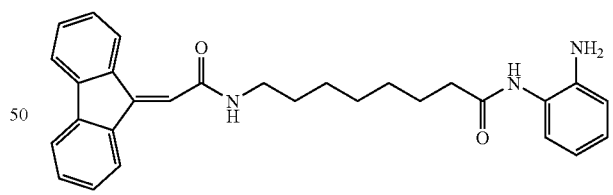

8-(2-(9H-fluoren-9-ylidene)acetamido)octanoic acid (363 mg, 1 mmol), and 8 ml of DMF were stirred at room temperature while 1-Ethyl-3-(3-dimethylaminopropyl)carbodiimide hydrochloride (394 mg, 2 mmol), hydroxy-benzotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (356 mg, 79% yield) as a brown solid. $^1$H NMR (DMSO-$d_6$) δ1.28 (m, 2H, $CH_2$), 1.34 (m, 4H, 2×$CH_2$), 1.51 (m, 2H, $CH_2$), 1.59 (m, 2H, $CH_2$), 2.30 (t, J=8.0 Hz, 2H, $CH_2CO$), 3.24 (m, 2H, $NCH_2$), 4.80 (s, 2H, benzene-NH2), 6.52 (t, J=8.0 Hz, 1H, Ar—H), 6.69 (d, J=8.0 Hz, 1H, Ar—H), 6.87 (t, J=8.0 Hz, 1H, Ar—H), 7.08 (s, 1H, =CH—CO), 7.13 (d, J=8.0 Hz, 1H, Ar—H), 7.31 (m, 2H, Ar—H), 7.41 (t, J=8.0 Hz, 2H, Ar—H), 7.76 (d, J=8.0 Hz, 1H, Ar—H), 7.81 (m, 2H, Ar—H), 8.52 (t, J=4.0 Hz, 1H, CONH), 8.67 (d, J=8.0 Hz, 1H, Ar—H), 9.09 (s, 1H, benzene-NH). LC-MS (m/z) 454 (M+1).

Example 29

Preparation of 6-(2-(5H-dibenzocyclohepten-5-ylidene)acetamido)hexanoic acid methyl ester

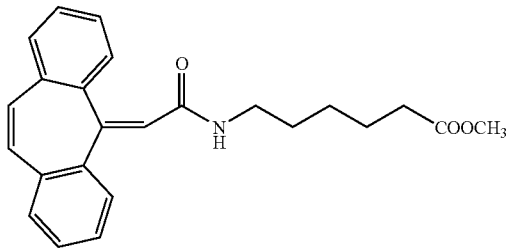

2-(5H-dibenzocyclohepten-b-ylidene)acetic acid (246 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and 6-aminocaproic acid methyl ester hydrochloride (219 mg, 1.2 mmol) were added. The mixture was stirred for 24 hours at room temperature. The mixture was diluted with 400 mL of brine. The solids were collected by vacuum filtration, washed with water and dried under vacuum to give the title compound (282 mg, 75% yield) as a white solid. LC-MS (m/z) 376 (M+1).

Example 30

Preparation of 6-(2-(5H-dibenzocyclohepten-5-ylidene)acetamido)hexanoic acid

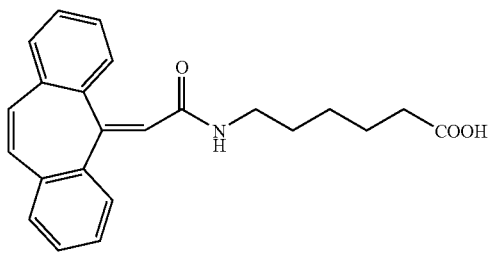

6-(2-(5H-dibenzocyclohepten-5-ylidene)acetamido)hexanoic acid methyl ester (375 mg, 1 mmol) and 300 ml of CH₃OH were stirred at room temperature while 25 ml of 4 N solution of LiOH in H₂O was added. The mixture was stirred for 24 hours at room temperature. The mixture was neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (310 mg, 86% yield) as a white solid. LC-MS (m/z) 362 (M+1).

Example 31

Preparation of 6-(2-(5H-dibenzocyclohepten-5-ylidene)acetamido)-N-hydroxyhexanamide

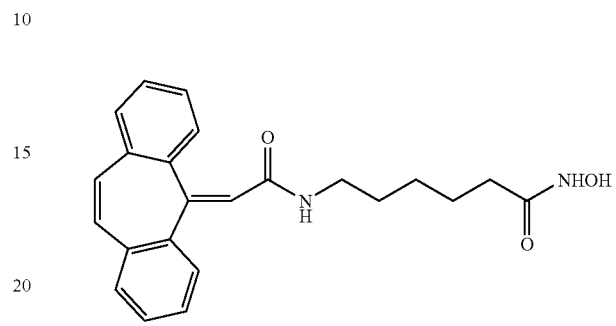

6-(2-(5H-dibenzocyclohepten-5-ylidene)acetamido)hexanoic acid (361 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (143 mg, 38%) as a yellow solid. LC-MS (m/z) 377 (M+1).

Example 32

Preparation of 6-(2-(10,11-dihydro-5H-dibenzocyclohepten-5-ylidene)acetamido)hexanoic acid methyl ester

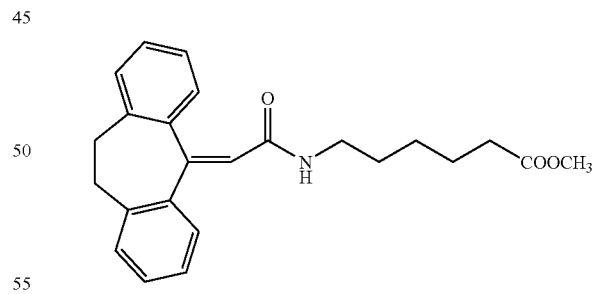

2-(10,11-dihydro-5H-dibenzocyclohepten-5-ylidene)acetic acid (250 mg, 1 mmol) and 8 ml of DMF were stirred at room temperature while 1-Ethyl-3-(3-dimethylaminopropyl)-carbodiimide hydrochloride (394 mg, 2 mmol), hydroxybenzo-triazole (162 mg, 1.2 mmol), triethylamine (404 mg, 4 mmol) and 6-aminocaproic acid methyl ester hydrochloride (219 mg, 1.2 mmol) were added. The mixture was stirred for 24 hours at room temperature. The mixture was diluted with 400 mL of brine. The solids were collected by vacuum filtration, washed with water and dried under

Example 33

Preparation of 6-(2-(10,11-dihydro-5H-dibenzocyclohepten-5-ylidene)acetamido)hexanoic acid

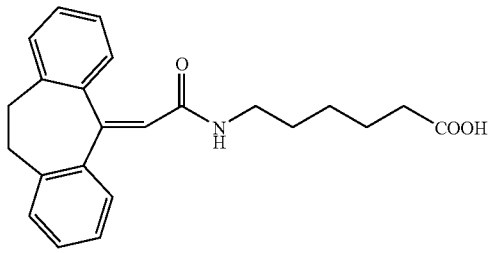

6-(2-(10,11-dihydro-5H-dibenzocyclohepten-5-ylidene)acetamido)hexanoic acid methyl ester (377 mg, 1 mmol) and 300 ml of $CH_3OH$ were stirred at room temperature while 25 ml of 4 N solution of LiOH in $H_2O$ was added. The mixture was stirred for 24 hours at room temperature. The mixture was neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (265 mg, 73% yield) as a white solid. LC-MS (m/z) 364 (M+1).

Example 34

Preparation of 6-(2-(10,11-dihydro-5H-dibenzocyclohepten-5-ylidene)acetamido)-N-hydroxyhexanamide

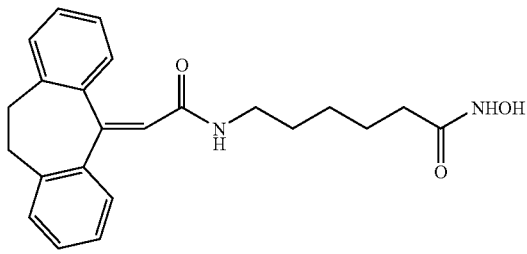

6-(2-(10,11-dihydro-5H-dibenzocyclohepten-5-ylidene)acetamido)hexanoic acid (363 mg, 1 mmol), triethylamine (151 mg, 1.5 mmol) and 20 ml of DMF were stirred at 0° C. while ethyl chloroformate (163 mg, 1.5 mmol) was added. The mixture was stirred at 0° C. for 2 hours, and then 50% aqueous solution of hydroxylamine (1.32 g, 20 mmol) was added. The mixture was stirred for 3 hours at room temperature, and then diluted with 1000 mL of brine. The solids were collected by vacuum filtration, washed with water and dried under vacuum to give the title compound (313 mg, 83% yield) as a white solid. LC-MS (m/z) 378 (M+1).

Example 35

Preparation of 6-(2-(9H-xanthen-9-ylidene)acetamido)hexanoic acid methyl ester

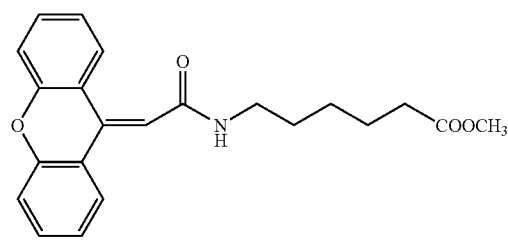

2-(9H-xanthen-9-ylidene)acetic acid (238 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and 6-aminocaproic acid methyl ester hydrochloride (219 mg, 1.2 mmol) were added. The mixture was stirred for 24 hours at room temperature. The mixture was diluted with 400 mL of brine. The solids were collected by vacuum filtration, washed with water and dried under vacuum to give the title compound (321 mg, 88% yield) as a white solid. LC-MS (m/z) 366 (M+1).

Example 36

Preparation of 6-(2-(9H-xanthen-9-ylidene)acetamido)hexanoic acid

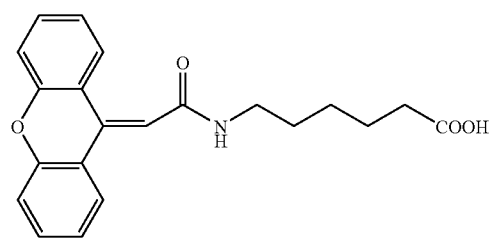

6-(2-(9H-xanthen-9-ylidene)acetamido)hexanoic acid methyl ester (365 mg, 1 mmol) and 300 ml of $CH_3OH$ were stirred at room temperature while 25 ml of 4 N solution of LiOH in $H_2O$ was added. The mixture was stirred for 24 hours at room temperature. The mixture was neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (178 mg, 47%) as a yellow solid. LC-MS (m/z) 379 (M+1).

Example 37

Preparation of 6-(2-(9H-xanthen-9-ylidene)aceta-mido)-N-(2-aminophenyl)hexanamide

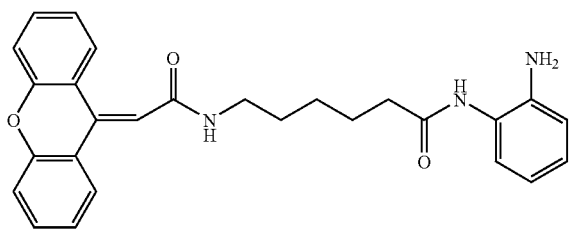

6-(2-(9H-xanthen-9-ylidene)acetamido)hexanoic acid (351 mg, 1 mmol), and 8 ml of DMF were stirred at room temperature while 1-Ethyl-3-(3-dimethylaminopropyl)car-bodiimide hydrochloride (394 mg, 2 mmol), hydroxy-benzo-triazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (335 mg, 76% yield) as a brown solid. LC-MS (m/z) 442 (M+1).

Example 38

Preparation of 6-(2-(9H-thioxanthen-9-ylidene)acetamido)hexanoic acid methyl ester

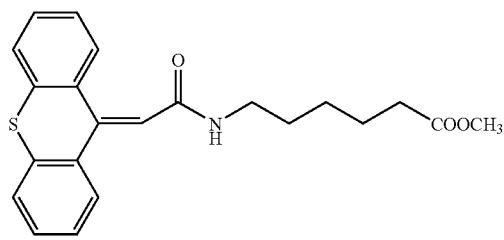

2-(9H-thioxanthen-9-ylidene)acetic acid (254 mg, 1 mmol) and 8 ml of DMF were stirred at room temperature while 1-Ethyl-3-(3-dimethylaminopropyl)carbodiimide hydrochloride (394 mg, 2 mmol), hydroxybenzo-triazole (162 mg, 1.2 mmol), triethylamine (404 mg, 4 mmol) and 6-aminocaproic acid methyl ester hydrochloride (219 mg, 1.2 mmol) were added. The mixture was stirred for 24 hours at room temperature. The mixture was diluted with 400 mL of brine. The solids were collected by vacuum filtration, washed with water and dried under vacuum to give the title compound (312 mg, 82% yield) as a white solid. LC-MS (m/z) 382 (M+1).

Example 39

Preparation of 6-(2-(9H-thioxanthen-9-ylidene)acetamido)hexanoic acid

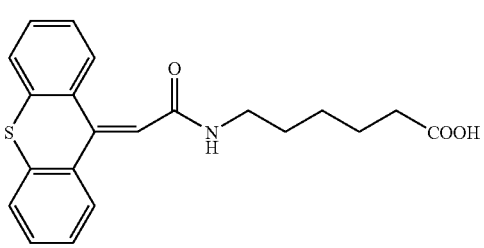

6-(2-(9H-thioxanthen-9-ylidene)acetamido)hexanoic acid methyl ester (381 mg, 1 mmol) and 300 ml of $CH_3OH$ were stirred at room temperature while 25 ml of 4 N solution of LiOH in $H_2O$ was added. The mixture was stirred for 24 hours at room temperature. The mixture was neutralized with concentrated hydrochloric acid to pH 7 and evaporated under vacuum to remove methanol. The residue was adjusted to pH 3 with concentrated hydrochloric acid. The solids were collected by vacuum filtration, washed with water and dried under vacuum to give the title compound (249 mg, 68% yield) as a white solid. LC-MS (m/z) 368 (M+1).

Example 40

Preparation of 6-(2-(9H-thioxanthen-9-ylidene)ac-etamido)-N-(2-aminophenyl)hexanamide

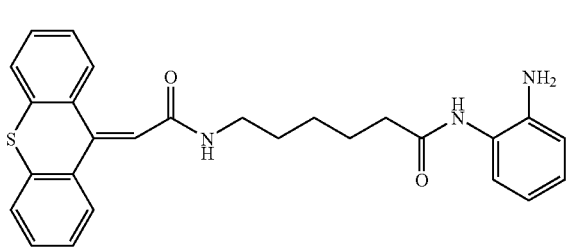

6-(2-(9H-thioxanthen-9-ylidene)acetamido)hexanoic acid (367 mg, 1 mmol), and 8 ml of DMF were stirred at room temperature while 1-Ethyl-3-(3-dimethylaminopropyl)car-bodi-imide hydrochloride (394 mg, 2 mmol), hydroxy-ben-zotriazole (162 mg, 1.2 mmol), triethylamine (404 mg, 4 mmol) and o-phenylenediamine (432 mg, 4 mmol) were added. The mixture was stirred for 24 hours at room temperature. The mixture was diluted with 400 mL of brine. The solids were collected by vacuum filtration, washed with water and dried under vacuum to give the title compound (302 mg, 66% yield) as a brown solid. LC-MS (m/z) 458 (M+1).

Example 41

In Vitro Inhibition of Total HDAC Enzyme Activity, in Cell Inhibition of HDAC Subtypes Activity by Reporter Gene, and in Cell Acetylation of α-Tubulin by Some Compounds of Formula (I)

| Example (compound) | % of Inhibition on total HDAC enzyme at 30 μM | % of SAHA Response for HDAC Class I at 10 μM (P21 reporter gene) | % of SAHA Response for HDAC3 at 10 μM (gdf11 reporter gene) | % of SAHA Response for HDAC4/5 at 10 μM (MEF2 reporter gene) | Fold of tubulin acetylation (HDAC7 at 10 μM | % of SAHA Response for HDAC7 at 10 μM (Nur77 reporter gene) |
|---|---|---|---|---|---|---|
| SAHA | 99% | 100% | 100% | 100% | 7.52 | 100% |
| 7 | 42% | 49% | 36% | 31% | nd | 19% |
| 8 | 31.7% | 16% | 10% | 30% | nd | 7% |
| 11 | 99% | 77% | 81% | 56% | 3.141 | 90% |
| 12 | 50% | 39% | 26% | 101% | 0.79 | 38% |
| 13 | 50% | 133% | 66% | 118% | 0.74 | 66% |
| 14 | 38.2% | 13% | 6% | 9% | nd | 4% |
| 15 | 42.4% | 21% | 14% | 15% | nd | 4% |
| 16 | 29.2% | 21% | 12% | 27% | nd | 10% |
| 17 | 24.1% | 12% | 7% | 21% | nd | 7% |
| 26 | 99.3% | 61% | 70% | 87% | nd | 89% |
| 27 | 42.3% | 18% | 12% | 16% | nd | 7% |
| 28 | 48% | 62% | 33% | 38% | nd | 20% | nd*: not determined
ia*: inactive

Measurement of In Vitro Inhibition of Total HDAC Enzyme Activity:

The in vitro inhibition of total HDAC enzyme was determined by HDAC Fluorimetric Assay/Drug Discovery Kit (BIOMOL) according to manufacture's instruction.

1. Add Assay buffer, diluted trichostatin A or test inhibitor to appropriate wells of the microtiter plate. Following table lists examples of various assay types and the additions required for each test.

| Sample | Assay Buffer | HeLa Extract (Dilution) | Inhibitor (5x) | Fluor de Lys ™ Substrate (2x) |
|---|---|---|---|---|
| Blank (No Enzyme) | 25 μl | 0 | 0 | 25 μl |
| Control | 10 μl | 15 μl | 0 | 25 μl |
| Trichostatin A | 0 | 15 μl | 10 μl | 25 μl |
| Test Sample | 0 | 15 μl | 10 μl | 25 μl |

2. Add diluted HeLa extract or other HDAC sample to all wells except those that are to be "No Enzyme Controls" (Blank).
3. Allow diluted Fluor de LYS™ Substrate and the samples in the microtiter plate to equilibrate to assay temperature (25° C.).
4. Initiate HDAC reactions by adding diluted substrate (25 μl) to each well and mixing thoroughly.
5. Allow HDAC reactions to proceed for desired length of time and then stop them by addition of Fluor de Lys™ Developer (50 μl). Incubate plate at room temperature (25° C.) for 10-15 min.
6. Read samples in a microtiter-plate reading fluorimeter capable of excitation at a wavelength in the range 350-380 nm and detection of emitted light in the range 440-460 nm.

Measurement of In Vivo Inhibition of HDAC Subtype Activity:

HDAC subtype selectivity inhibition assay of tested compounds was carried out by several reporter gene assays experiments. Briefly, HeLa cells were seeded in 96-well plates the day before transfection to give a confluence of 50-80%. Cells were transfected with one of reporter gene plasmids containing a promoter sequences or response elements upstream of a luciferase gene construct using FuGene6 transfection reagent according to the manufacturer's instructions (Roche). The promoter or response elements including p21-promoter, gdf11-promoter, serum response element (SRE), MEF-binding element were fused upstream to the luciferase gene reporter construct. For normalizing the transfection efficiency, a GFP expression plasmid was cotransfected. Cells were allowed to express protein for 24 hours followed by addition of individual compounds or the vehicle (DMSO). 24 hours later the cells were harvested, and the luciferase assays were performed using the luciferase assay kit according to the manufacturer's instructions (Promega). To normalize the data from the luciferase assays, β-galactosidase activity from transfected cells was measured using a kit (Promega) as instructed by the manufacturer.

Measurement of In Vivo Acetylation Activity on Substrates: Cytoblot Assay of Acetylation α-tubulin This assay is used to measure in vivo inhibition of HDAC6 in a cytoblot assay.

Materials and Reagent:
1. 96-well tissue culture white plate
2. A549 cell line
3. Anti-acetyl-tubulin (Upstate)
4. HRP-labeled anti-mouse IgG (Upstate)
5. Fixation solution: 95% ethanol, 5% acetic acid
6. TBS: 0.15M NaCl, 0.02M Tris-Cl pH7.4
7. ADB: TBS+2% BSA+0.1% Triton X-100
8. Enhanced chemiluminescence (ECL) (Amersham)

Procedure for Performing the Assay in 96-Well Plate:
1. A549 cells were seeded at a density of 20000 cells/200 μl/well in 96-well white plate and incubated at 37° C. for 24 hours.
2. Compounds were added and incubated for 24 hours at 37° C.
3. After incubation with test compounds, culture medium was removed, then add 100 μl/well of fixation solution for 5 min.
4. Wells were aspirated and washed twice with ADB.

5. After aspirating, 100 μl/well of ADB containing anti-Ac-tubulin (1:200) were added and incubated for 2 hour at room temperature.
6. Wells were aspirated and washed twice with 150 μl ADB.
7. After aspirating, 100 μl/well of IgG-HRP conjugated antibody (1:1000) were added and incubated for 2 hour at room temperature.
8. Plates were washed three times with 150 μl TBS.
9. Add 50 μl/well of ECL mixture, then plates were read on the plate reader.

Cytoblot Assay of Acetylation Lysine

This assay is used to measure the in vivo inhibition of total HDAC activity in a cytoblot assay.

Materials and Reagent:
9. 96-well tissue culture white plate
10. A549 cell line
11. Anti-acetyl-lysine (Upstate)
12. HRP-labeled anti-mouse IgG (Upstate)
13. Fixation solution: 95% ethanol, 5% acetic acid
14. TBS: 0.15M NaCl, 0.02M Tris-Cl pH7.4
15. ADB: TBS+2% BSA+0.1% Triton X-100
16. Enhanced chemiluminescence (ECL) (Amersham)

Procedure for Performing the Assay in 96-Well Plate:
10. A549 cells were seeded at a density of 20000 cells/200 μl/well in 96-well white plate and incubated at 37° C. for 24 hours.
11. Compounds were added and incubated for 24 hours at 37° C.
12. After incubation with test compounds, culture medium was removed, then add 100 μl/well of fixation solution for 5 min.
13. Wells were aspirated and washed twice with ADB.
14. After aspirating, 100 μl/well of ADB containing anti-Ac-lysine (1:200) were added and incubated for 2 hour at room temperature.
15. Wells were aspirated and washed twice with 150 μl ADB.
16. After aspirating, 100 μl/well of IgG-HRP conjugated antibody (1:1000) were added and incubated for 2 hour at room temperature.
17. Plates were washed three times with 150 μl TBS.
18. Add 50 μl/well of ECL mixture, then plates were read on the analyst plate reader.

Example 42

| Example (compound) | GI$_{50}$ μM (Hut-78) | GI$_{50}$ μM (HL60) | GI$_{50}$ μM (HeLa) | GI$_{50}$ μM (A549) |
|---|---|---|---|---|
| 11 | <0.1 | <0.1 | 0.52 | 2.34 |
| 12 | 3.89 | 2.29 | 22.91 | 18.20 |
| 13 | 1.35 | 1.35 | 8.32 | 4.90 |

Measurement of In Vivo Cell Proliferation:

Tumor cells were trypsinized and plated into 96-well plates at 3,000 per well and incubated in complete medium with 10% FBS for 24 hours. Compounds were added over a final concentration range of 100 μmol/L to 100 nmol/L in 0.1% DMSO and incubated for 72 hours in complete medium. The effects on proliferation were determined by addition of MTS reagent (Promega) according to the instruction, incubation for 2 hours at 37° C. in CO$_2$ incubator, and record the absorbance at 490 nm using an ELISA plate reader.

What is claimed is:

1. A compound of formula I:

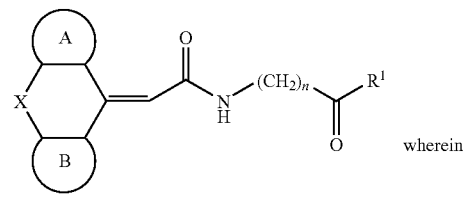

wherein

X is a bond, —CH2CH2-, —CH═CH—, O or S;

Ring A and ring B, fused to the ring containing X, independently of each other represents a benzene ring, which optionally substituted with one or more halogen, nitro, alkyl, alkoxy or amino;

R$^1$ is

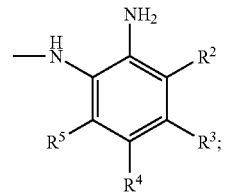

R$^2$, R$^3$, R$^4$ and R$^5$ are independently hydrogen, halo, alkyl, alkoxy or trifluoromethyl;

n is an integer ranging from 1 to 7.

2. A compound of claim 1, wherein

X is a bond, —CH$_2$CH$_2$—, —CH═CH—, O or S;

Ring A and ring B, fused to the ring containing X, independently of each other represents a benzene ring;

R$^1$ is

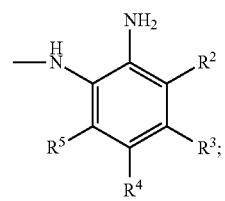

R$^2$, R$^3$, R$^4$ and R$^5$ are independently hydrogen, halo, alkyl, alkoxy or trifluoromethyl;

n is an integer ranging from 4 to 7.

3. A compound of claim 1, wherein

X is a bond;

Ring A and ring B, fused to the ring containing X, independently of each other represents a benzene ring;

R¹ is

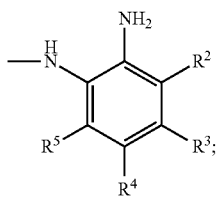

R², R³, R⁴ and R⁵ are independently hydrogen, halo, alkyl, alkoxy or trifluoromethyl;

n is an integer ranging from 4 to 7.

4. A pharmaceutical composition comprising an effective amount of a compound according to claim 1 and at least one pharmaceutically acceptable excipient, carrier or diluent.

5. A method of treatment of at least one disease selected from the group consisting of Rubinstein-Taybi syndrome, fragile X syndrome, leukemia, and lung cancer, comprising administering to a subject in need thereof an effective amount of a compound according to claim 1.

6. A method of treatment of at least one disease selected from the group consisting of stroke, Huntington's disease, and Amyotrophic Lateral Sclerosis, comprising administering to a subject in need thereof an effective amount of a compound according to claim 1.

7. A dosage form unit of the pharmaceutical composition of claim 4 comprising an amount within the range of about 0.0001 to about 200 mg of said compound.

8. A pharmaceutical composition of claim 4 which is suitable for administration by the oral, nasal, transdermal, pulmonary, or parenteral route.

9. A method comprising inhibiting histone deacetylase in a cell with an effective amount of a compound according to claim 1.

* * * * *